US006783973B1

(12) United States Patent
Bunzow et al.

(10) Patent No.: US 6,783,973 B1
(45) Date of Patent: Aug. 31, 2004

(54) MAMMALIAN CATECHOLAMINE RECEPTOR GENES AND USES

(75) Inventors: James R. Bunzow, Portland, OR (US); David K. Grandy, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 243 days.

(21) Appl. No.: 09/659,519

(22) Filed: Sep. 12, 2000

(51) Int. Cl.[7] .......................... C12P 21/06; C12N 15/06; C12N 15/12; C12N 5/06; C12N 1/20
(52) U.S. Cl. .............................. 435/252.3; 435/320.1; 435/325; 435/69.1; 536/23.5
(58) Field of Search ............................ 435/69.1, 320.1, 435/325, 252.3; 536/23.5; 530/350

(56) References Cited

U.S. PATENT DOCUMENTS

| | | |
|---|---|---|
| 5,422,265 A | 6/1995 | Civelli et al. |
| 5,427,942 A | 6/1995 | Civelli et al. |
| 5,569,601 A | 10/1996 | Civelli et al. |
| 5,594,108 A | 1/1997 | Civelli et al. |
| 5,686,573 A | 11/1997 | Civelli et al. |
| 5,880,260 A | 3/1999 | Civelli et al. |
| 5,883,226 A | 3/1999 | Civelli et al. |

FOREIGN PATENT DOCUMENTS

| | | |
|---|---|---|
| EP | 0 859 055 A | 8/1998 |
| WO | WO 00 73449 A | 12/2000 |
| WO | WO 01 36473 A | 5/2001 |
| WO | WO 01 72841 A | 10/2001 |

OTHER PUBLICATIONS

Skolnick et al., 2000, Trends in Biotech. 18:34–39.*
Bork, P., 2000, Genome Research 10:398–400.*
Doerks et al., 1998, Trends in Genetics 14:248–250.*
Smith et al., 1997, Nature Biotechnology 15:1222–1223.*
Brenner, S., 1999, Trends in Genetics 15:132–133.*
Bork et al., 1996, Trends in Genetics 12:425–427.*
Ji, et al, 1998, JBC, 273:17299–17302.*
Probst, et al, 1992, DNA and Cell Biol. 11(1): 1–20.*
Barowsky, et al, 2001, Accession No. AF380185__1.*
Bunzow, et al 2001, Mol. Pharmacol., 60: 1181–1188.*
Amlaiky and Caron, "Identification of the $D_2$–Dopamine Receptor Binding Subunit in Several Mammalian Tissues and Species by Photoaffinity Labeling," *J. Neurochem.* 47, 196–204 (1986).
Amlaiky and Caron, "Photoaffinity Labeling of the $D_2$–dopamine Receptor Using a Novel High Affinity Radio-iodinated Probe," *J. Biol Chem.* 260, 1983–1986 (1985).
Amlaiky et al., "Identification of the Binding Subunit of the $D_1$–Dopamine Receptor by Photoaffinity Crossliking," *Mol. Pharmacol.* 31, 129–134 (1987).
Bunzow et al., "Cloning and expression of a rat $D_2$ dopamine receptor cDNA," *Nature* 336, 783–787 (1988).
Chirgwin et al., "Isolation of Biologically Active Ribonucleic Acid from Sources Enriched in Ribonuclease," 1979, Biochemistry 5294–5299.

Cooper et al., "Catecholamines II: CNS Aspects," in *The Biochemical Basis of Neuropharmacology,* 3d ed. 1978 (Oxford University Press, N.Y.), pp. 161–195.
Civelli et al., Ann. Rev. Pharmacol. Toxicol. 1993, 32:281–307.
Cotecchia et al., Proc. Natl. Acad. Sci., vol. 85, pp. 7159–7163.
Dal Toso et al. EMBO J. 8, 4025–4034 (1989).
Dixon et al., Nature 321, 75–79 (1986).
Dixon et al., Annual Reports in Medicinal Chemistry, 23: 221–233.
Eisenberg et al., J. Mol. Biol. (1984) 179, 125–142.
Emorine et al., Proc. Natl. Acad. Sci. 84:6995–6999.
Frielle et al., Proc. Natl. Acad. Sci. (1987) 34:7920–7924.
Gingrich et al., *J Biochemistry* 27, 3907–3912 (1988).
Grandy et al., "Cloning of the cDNA and gene for human $D_2$ dopamine receptor," *Proc. Natl. Acad. Sci.* USA 86, 9762–9766 (1989).
Hoffman et al., Ann. Rev. Physiol. 1982 44:475–84.
Jarvie et al., "Dopamine $D_2$ Receptor Binding Subunits of $M_r \cong 140,000$ and 94,000 in Brain: Deglycosylation Yields a Common Unit of $M_r \cong 44,000$," *Mol. Pharmacol.* 34, 91–97 (1988).
Kebabian and Calne, "Multiple receptors for dopamine," *Nature* 277, 93–96 (1979).
Kobilka, B. K. Science 238:650–656 (1987).
Probst et al., DNA and Cell Biology 11:No. 1, 1992 pp. 1–20.
Saiki et al., Science vol. 239 487–491.
Sanger et al., "DNA sequencing with chain–terminating inhibitors," *Proc. Natl. Acad. Sci. USA* 74(12), 5463–5467 (1977).

(List continued on next page.)

*Primary Examiner*—Elizabeth Kemmerer
*Assistant Examiner*—Sandra Wegert
(74) *Attorney, Agent, or Firm*—McDonnell Boehnen Hulbert & Berghoff

(57) ABSTRACT

The present invention relates to novel mammalian catecholamine receptor proteins and genes that encode such proteins. The invention is directed toward the isolation and characterization of mammalian catecholamine receptor proteins. The invention specifically provides isolated complementary DNA copies of mRNA corresponding to rat and human homologues of a mammalian catecholarnine receptor gene. Also provided are recombinant expression constructs capable of expressing the mammalian catecholamine receptor genes of the invention in cultures of transformed prokaryotic and eukaryotic cells, as well as such cultures of transformed cells that synthesize the mammalian catecholamine receptor proteins encoded therein. The invention also provides methods for screening compounds in vitro that are capable of binding to the mammalian catecholamine receptor proteins of the invention, and further characterizing the binding properties of such compounds in comparison with known catecholamine receptor agonists and antagonists. Improved methods of pharmacological screening are provided thereby.

7 Claims, 13 Drawing Sheets

OTHER PUBLICATIONS

Seeman, *Synapse* 1, 133–152 (1987).

Sengoles et al., "Purification and Characterization of the $D_2$–Dopamine Receptor from Bovine Anterior Pituitary," *J. Biol. Chem.* 263, 18996–19002 (1988).

Senogles et al., *American Chemical Society* 25, 749–753 (1986).

Smithies et al., "Insertion of DNA sequences into the human chromosomal β–globin locus by homologous recombination," *Nature* 317, 230–234 (1985).

Sokoloff et al., "Molecular cloning and characterization of a novel dopamine receptor ($D_3$) as a target for neuroleptics," *Nature* 347, 146–151 (1990).

Sunahara et al., "Human dopamine $D_1$ receptor encoded by an intronless gene on chromosome 5," *Nature* 347, 80–83 (1990).

Van Tol et al., "Cloning of the gene for a human dopamine D4 receptor with high affinity for the antipsychotic clozapine," *Nature* 350, 610–614 (1991).

Zhou et al., "Cloning and expression of human and rat $D_1$ dopamine receptors," *Nature* 347, 76–80 (1990).

Bunzow et al., "Amphetamine 3,4–Methylenedioxymethamphetamine, lysergic acid diethylamide, and metabolites of the catecholamine neurotransmitters are agonists of a rat trace amine receptor," *Molecular Pharmacology.* 60(6): 1181–1188 (Dec. 2001).

Borowsky et al., "Trace amines: Identification of a family of mammalian G protein–coupled receptors," *Proc. Nat. Acad. Sci. of U.S.A.* 98(16): 8966–8971 (Jul. 31, 2001).

Lee et al., "Cloning and Characterization of Additional Members of the G Protein–Coupled Receptor Family," *Biochimica et Biophysica Acta.* 1490(2000):311–23.

Singewald et al., "Involvement of biogenic amines and amino acids in the central regulation of cardiovascular homeostasis," *Trends in Pharmacological Sciences.* 17 (10):356–63 (1996).

Szikra et al., "Receptor Binding Properties of Hemorphin Analogue in Rat Brain Membrane Preparations," *Neurobiology.* 4(3):279–80 (1996).

Zeng et al., "Cloning of a putative human neurotransmitter receptor expressed in skeletal muscle and brain," *Biochemical and Biophysical Research Communications.* 242(3):575–78(1998).

* cited by examiner

Figure 1

```
              10         20        29         38        47         56
                         >__      ___ ___ ___ ___ ___ ___ ___ ___ ___ ___
CTAATTGACA GCCCTCAGGA   ATG ATG CCC TTT TGC CAC AAT ATA ATT AAT ATT TCC
                       MET MET Pro Phe Cys His Asn Ile Ile Asn Ile Ser 65         74        83         92        101        110
___ ___ ___ ___ ___ ___ ___ ___ ___ ___ ___ ___ ___ ___ ___ ___
TGT GTG AAA AAC AAC TGG TCA AAT GAT GTC CGT GCT TCC CTG TAC AGT TTA ATG
Cys Val Lys Asn Asn Trp Ser Asn Asp Val Arg Ala Ser Leu Tyr Ser Leu MET 119        128       137        146       155        164
___ ___ ___ ___ ___ ___ ___ ___ ___ ___ ___ ___ ___ ___ ___ ___
GTG CTC ATA ATT CTG ACC ACA CTC GTT GGC AAT CTG ATA GTT ATT GTT TCT ATA
Val Leu Ile Ile Leu Thr Thr Leu Val Gly Asn Leu Ile Val Ile Val Ser Ile 173        182       191        200       209        218
___ ___ ___ ___ ___ ___ ___ ___ ___ ___ ___ ___ ___ ___ ___ ___
TCA CAC TTC AAA CAA CTT CAT ACC CCA ACA AAT TGG CTC ATT CAT TCC ATG GCC
Ser His Phe Lys Gln Leu His Thr Pro Thr Asn Trp Leu Ile His Ser MET Ala 227        236       245        254       263·       272
___ ___ ___ ___ ___ ___ ___ ___ ___ ___ ___ ___ ___ ___ ___ ___
ACT GTG GAC TTT CTT CTG GGG TGT CTG GTC ATG CCT TAC AGT ATG GTG AGA TCT
Thr Val Asp Phe Leu Leu Gly Cys Leu Val MET Pro Tyr Ser MET Val Arg Ser 281        290       299        308       317        326
___ ___ ___ ___ ___ ___ ___ ___ ___ ___ ___ ___ ___ ___ ___ ___
GCT GAG CAC TGT TGG TAT TTT GGA GAA GTC TTC TGT AAA ATT CAC ACA AGC ACC
Ala Glu His Cys Trp Tyr Phe Gly Glu Val Phe Cys Lys Ile His Thr Ser Thr 335        344       353        362       371        380
___ ___ ___ ___ ___ ___ ___ ___ ___ ___ ___ ___ ___ ___ ___ ___
GAC ATT ATG CTG AGC TCA GCC TCC ATT TTC CAT TTG TCT TTC ATC TCC ATT GAC
Asp Ile MET Leu Ser Ser Ala Ser Ile Phe His Leu Ser Phe Ile Ser Ile Asp 389        398       407        416       425        434
___ ___ ___ ___ ___ ___ ___ ___ ___ ___ ___ ___ ___ ___ ___ ___
CGC TAC TAT GCT GTG TGT GAT CCA CTG AGA TAT AAA GCC AAG ATG AAT ATC TTG
Arg Tyr Tyr Ala Val Cys Asp Pro Leu Arg Tyr Lys Ala Lys MET Asn Ile Leu 443        452       461        470       479        488
___ ___ ___ ___ ___ ___ ___ ___ ___ ___ ___ ___ ___ ___ ___ ___
GTT ATT TGT GTG ATG ATC TTC ATT AGT TGG AGT GTC CCT GCT GTT TTT GCA TTT
Val Ile Cys Val MET Ile Phe Ile Ser Trp Ser Val Pro Ala Val Phe Ala Phe 497        506       515        524       533        542
___ ___ ___ ___ ___ ___ ___ ___ ___ ___ ___ ___ ___ ___ ___ ___
GGA ATG ATC TTT CTG GAG CTA AAC TTC AAA GGC GCT GAA GAG ATA TAT TAC AAA
Gly MET Ile Phe Leu Glu Leu Asn Phe Lys Gly Ala Glu Glu Ile Tyr Tyr Lys 551        560       569        578       587        596
___ ___ ___ ___ ___ ___ ___ ___ ___ ___ ___ ___ ___ ___ ___ ___
CAT GTT CAC TGC AGA GGA GGT TGC TCT GTC TTC TTT AGC AAA ATA TCT GGG GTA
His Val His Cys Arg Gly Gly Cys Ser Val Phe Phe Ser Lys Ile Ser Gly Val 605        614       623        632       641        650
___ ___ ___ ___ ___ ___ ___ ___ ___ ___ ___ ___ ___ ___ ___ ___
CTG ACC TTT ATG ACT TCT TTT TAT ATA CCT GGA TCT ATT ATG TTA TGT GTC TAT
Leu Thr Phe MET Thr Ser Phe Tyr Ile Pro Gly Ser Ile MET Leu Cys Val Tyr
```

```
              659         668         677         686         695         704
          ___ ___ ___ ___ ___ ___ ___ ___ ___ ___ ___ ___ ___ ___ ___ ___
          TAC AGA ATA TAT CTT ATC GCT AAA GAA CAG GCA AGA TTA ATT AGT GAT GCC AAT
          Tyr Arg Ile Tyr Leu Ile Ala Lys Glu Gln Ala Arg Leu Ile Ser Asp Ala Asn 713         722         731         740         749         758
          ___ ___ ___ ___ ___ ___ ___ ___ ___ ___ ___ ___ ___ ___ ___ ___
          CAG AAG CTC CAA ATT GGA TTG GAA ATG AAA AAT GGA ATT TCA CAA AGC AAA GAA
          Gln Lys Leu Gln Ile Gly Leu Glu MET Lys Asn Gly Ile Ser Gln Ser Lys Glu 767         776         785         794         803         812
          ___ ___ ___ ___ ___ ___ ___ ___ ___ ___ ___ ___ ___ ___ ___ ___
          AGG AAA GCT GTG AAG ACA TTG GGG ATT GTG ATG GGA GTT TTC CTA ATA TGC TGG
          Arg Lys Ala Val Lys Thr Leu Gly Ile Val MET Gly Val Phe Leu Ile Cys Trp 821         830         839         848         857         866
          ___ ___ ___ ___ ___ ___ ___ ___ ___ ___ ___ ___ ___ ___ ___ ___
          TGC CCT TTC TTT ATC TGT ACA GTC ATG GAC CCT TTT CTT CAC TAC ATT ATT CCA
          Cys Pro Phe Phe Ile Cys Thr Val MET Asp Pro Phe Leu His Tyr Ile Ile Pro 875         884         893         902         911         920
          ___ ___ ___ ___ ___ ___ ___ ___ ___ ___ ___ ___ ___ ___ ___ ___
          CCT ACT TTG AAT GAT GTA TTG ATT TGG TTT GGC TAC TTG AAC TCT ACA TTT AAT
          Pro Thr Leu Asn Asp Val Leu Ile Trp Phe Gly Tyr Leu Asn Ser Thr Phe Asn 929         938         947         956         965         974
          ___ ___ ___ ___ ___ ___ ___ ___ ___ ___ ___ ___ ___ ___ ___ ___
          CCA ATG GTT TAT GCA TTT TTC TAT CCT TGG TTT AGA AAA GCA CTG AAG ATG ATG
          Pro MET Val Tyr Ala Phe Phe Tyr Pro Trp Phe Arg Lys Ala Leu Lys MET MET 983         992         1001        1010        1019        1028
          ___ ___ ___ ___ ___ ___ ___ ___ ___ ___ ___ ___ ___ ___ ___ ___
          CTG TTT GGT AAA ATT TTC CAA AAA GAT TCA TCC AGG TGT AAA TTA TTT TTG GAA
          Leu Phe Gly Lys Ile Phe Gln Lys Asp Ser Ser Arg Cys Lys Leu Phe Leu Glu 1037        1050        1060        1070        1080        1090
          ___ ___ ___ ___
                     ___>
          TTG AGT TCA TAG AATTATTATA TTTTACTGTT TTGCAAATCG GTTGATGATC ATATTTATGA
          Leu Ser Ser 1100        1110        1120
          ACACAACATA ACGAACCACA TGCACCAACC ACATG
```

```
                                  27                                              54
ATG CAT CTT TGC CAC AAT AGC GCG AAT ATT TCC CAC ACG AAC AGG AAC TGG TCA
MET His Leu Cys His Asn Ser Ala Asn Ile Ser His Thr Asn Arg Asn Trp Ser 81                                             108
AGG GAT GTC CGT GCT TCA CTG TAC AGC TTA ATA TCA CTC ATA ATT CTA ACC ACT
Arg Asp Val Arg Ala Ser Leu Tyr Ser Leu Ile Ser Leu Ile Ile Leu Thr Thr 135                                             162
CTG GTT GGC AAC TTA ATA GTA ATC ATT TCG ATA TCC CAC TTC AAG CAA CTT CAC
Leu Val Gly Asn Leu Ile Val Ile Ile Ser Ile Ser His Phe Lys Gln Leu His 189                                             216
ACG CCC ACA AAT TGG CTC CTT CAT TCC ATG GCC GTT GTC GAC TTT CTG CTG GGC
Thr Pro Thr Asn Trp Leu Leu His Ser MET Ala Val Val Asp Phe Leu Leu Gly 243                                             270
TGT CTG GTC ATG CCC TAC AGC ATG GTG AGA ACA GTT GAG CAC TGC TGG TAC TTT
Cys Leu Val MET Pro Tyr Ser MET Val Arg Thr Val Glu His Cys Trp Tyr Phe 297                                             324
GGG GAA CTC TTC TGC AAA CTT CAC ACC AGC ACT GAT ATC ATG CTG AGC TCG GCA
Gly Glu Leu Phe Cys Lys Leu His Thr Ser Thr Asp Ile MET Leu Ser Ser Ala 351                                             378
TCC ATT CTC CAC CTA GCC TTC ATT TCC ATT GAC CGC TAC TAT GCT GTG TGC GAC
Ser Ile Leu His Leu Ala Phe Ile Ser Ile Asp Arg Tyr Tyr Ala Val Cys Asp 405                                             432
CCT TTA AGA TAC AAA GCC AAG ATC AAT CTC GCC GCC ATT TTT GTG ATG ATC CTC
Pro Leu Arg Tyr Lys Ala Lys Ile Asn Leu Ala Ala Ile Phe Val MET Ile Leu 459                                             486
ATT AGC TGG AGC CTT CCT GCT GTT TTT GCA TTT GGG ATG ATC TTC CTG GAG CTG
Ile Ser Trp Ser Leu Pro Ala Val Phe Ala Phe Gly MET Ile Phe Leu Glu Leu 513                                             540
AAC TTA GAA GGA GTT GAG GAG CAG TAT CAC AAT CAG GTC TTC TGC CTG CGC GGC
Asn Leu Glu Gly Val Glu Glu Gln Tyr His Asn Gln Val Phe Cys Leu Arg Gly 567                                             594
TGT TTT CTA TTC TTC AGT AAA GTA TCT GGG GTA CTG GCA TTC ATG ACG TCT TTC
Cys Phe Leu Phe Phe Ser Lys Val Ser Gly Val Leu Ala Phe MET Thr Ser Phe 621                                             648
TAT ATA CCT GGG TCT GTT ATG TTA TTT GTT TAC TAT AGA ATA TAT TTC ATA GCT
Tyr Ile Pro Gly Ser Val MET Leu Phe Val Tyr Tyr Arg Ile Tyr Phe Ile Ala
```

```
                                              675                                         702
AAA GGA CAA GCG AGG TCA ATT AAT CGT GCA AAC CTT CAA GTT GGA TTG GAA GGG
Lys Gly Gln Ala Arg Ser Ile Asn Arg Ala Asn Leu Gln Val Gly Leu Glu Gly 729                                         756
GAA AGC AGA GCG CCA CAA AGC AAG GAA ACA AAA GCC GCG AAA ACC TTA GGG ATC
Glu Ser Arg Ala Pro Gln Ser Lys Glu Thr Lys Ala Ala Lys Thr Leu Gly Ile 783                                         810
ATG GTG GGC GTT TTC CTC CTG TGC TGG TGC CCG TTC TTT TTC TGC ATG GTC CTG
MET Val Gly Val Phe Leu Leu Cys Trp Cys Pro Phe Phe Phe Cys MET Val Leu 837                                         864
GAC CCT TTC CTG GGC TAT GTT ATC CCA CCC ACT CTG AAT GAC ACA CTG AAT TGG
Asp Pro Phe Leu Gly Tyr Val Ile Pro Pro Thr Leu Asn Asp Thr Leu Asn Trp 891                                         918
TTC GGG TAC CTG AAC TCT GCC TTC AAC CCG ATG GTT TAT GCC TTT TTC TAT CCC
Phe Gly Tyr Leu Asn Ser Ala Phe Asn Pro MET Val Tyr Ala Phe Phe Tyr Pro 945                                         972
TGG TTC AGA AGA GCG TTG AAG ATG GTT CTC TTC GGT AAA ATT TTC CAA AAA GAT
Trp Phe Arg Arg Ala Leu Lys MET Val Leu Phe Gly Lys Ile Phe Gln Lys Asp

999
TCA TCT AGG TCT AAG TTA TTT TTG TAA
Ser Ser Arg Ser Lys Leu Phe Leu
```

```
  1 MMPFCHNIINISCVKNNWSNDVRASLYSLMVLIILTTLVGNLIVIVSISH  50
    |  |||  |||    |||  |||||||||.  ||||||||||||:||||
  1 .MELCHNSANISHTNRNWSRDVRASLYSLISLIILTTLVGNLIVIISISH  49

51 FKQLHTPTNWLIHSMATVDFLLGCLVMPYSMVRSAEHCWYFGEVFCKIHT 100
    |||||||||||:||||.||||||||||||||||.|||||||.|||:||
 50 FKQLHTPTNWLLHSMAVVDFLLGCLVMPYSMVRTVEHCWYFGELFCKLHT  99

101 STDIMLSSASIFHLSFISIDRYYAVCDPLRYKAKMNILVICVMIFISWSV 150
    |||||||||| ||-|||||||||||||||||||||.|:  | ||| ||||.
100 STDIMLSSASILHLAFISIDRYYAVCDPLRYKAKINLAAIFVMILISWSL 149

151 PAVFAFGMIFLELNFKGAEEIYYKHVHCRGGCSVFFSKISGVLTFMTSFY 200
    |||||||||||||| .| || |:   | |  || .||||:|||| ||||||
150 PAVFAFGMIFLELNLEGVESQYHNQVFCLRGCFLFFSKVSGVLAFMTSFY 199

201 IPGSIMLCVYYRIYLIAKEQARLISDANQKLQIGLEMKNGISQSKERKAV 250
    ||||:|| ||||||  ||| |||  |.  ||   ||:|||  ..   |||| ||
200 IPGSVMLFVYYRIYFIAKGQARSINRAN..LQVGLEGESRAPQSKETKAA 247

251 KTLGIVMGVFLICWCPFFICTVMDPFLHYIIPPTLNDVLIWFGYLNSTFN 300
    |||||..||||:||||||| | |:|||| |:|||||||| | |||||||| ||
248 KTLGIMVGVFLLCWCPFFFCMVLDPFLGYVIPPTLNDTLNWFGYLNSAFN 297

301 PMVYAFFYPWFRKALKMMLFGKIFQKDSSRCKLFLELSS* 340
    |||||||||||||:||||.||||||||||| ||||
298 PMVYAFFYPWFRRALKMVLFGKIFQKDSSRSKLFL*.... 333
```

Northern Blot of Total RNA from HEK293 Cells Expressing pch2-3RC/RSVneo (the human cDNA)

MAMMALIAN CATECHOLAMINE RECEPTOR GENES AND USES

This invention was made with government support under National Institute of Health grants DA08562. The government has certain rights to this invention.

BACKGROUND OF THE INVENTION

1. Field of the Invention

This invention relates to catecholamine receptors from mammalian species and the genes corresponding to such receptors. Specifically, the invention relates to the isolation, cloning and sequencing of complementary DNA (cDNA) copies of messenger RNA (mRNA) encoding a novel mammalian catecholamine receptor gene. The invention also relates to the construction of recombinant expression constructs comprising cDNA of this novel catecholamine receptor gene, said recombinant expression constructs being capable of expressing catecholamine receptor protein in cultures of transformed prokaryotic and eukaryotic cells. Production of the receptor protein in such cultures is also provided. The invention relates to the use of such cultures of such transformed cells to produce homogeneous compositions of the novel catecholamine receptor protein. The invention also provides cultures of such cells producing this catecholamine receptor protein for the characterization of novel and useful drugs. Antibodies against and epitopes of this novel catecholamine receptor protein are also provided by the invention.

2. Background of the Invention

Catecholamines are a class of naturally-occurring amino acid derivatives having a variety of physiological effects in the peripheral and central nervous systems. The parent compound is β-phenylethylamine, and the catecholamines are derivatives of this parent compound. In addition to the naturally-occurring members of the class (epinephrine, norepinephrine and dopamine), a large number of synthetic compounds having biological activity have been developed and have utility as drugs (including albuterol, isoproterenol, propranolol, phenylephrine, amphetamine and methamphetamine). In the periphery, catecholamines are released by the sympathetic nervous system and adrenal medulla and are involved in integrating physiological responses to stress, while in the central nervous system the catecholamines constitute some of the most important neurotransmitter systems.

The effect of catecholamines are mediated through their receptors and their associated cell signaling systems (reviewed in Hoffman & Lefkowitz, 1982, Ann. Rev. Physiol. 44: 475–484; Civelli et al., 1993, Ann. Rev. Pharm. & Tox. 33: 281–307). These receptors are located in the plasma membrane of catecholamine-sensitive cells. Structurally, they are characterized by having a pattern of seven transmembrane domains (see,for example, U.S. Pat. Nos. 5,422,265,5,569,601, 5,594,108,5,883,226, 5,880,260, 5,427,942 and 5,686,573). Functionally, certain of these receptors interact with adenylate cyclase, either stimulating or inhibiting the production of cyclic AMP thereby. These receptors include the adrenergic receptors (the a-1, a-2, b-1, b-2, and b-3 adrenergic receptors) and the dopamine receptors (the $D_1$-, $D_2$-, $D_3$-, $D_{-4}$-, and $D_5$-dopamine receptors).

For example, epinephrine (adrenaline) and norepinephrine, as well as synthetic agonists of these catecholamines which mimic their biological functions, and antagonists which block these biological functions, exert their effects by binding to specific recognition sites (membrane receptors) situated on the cell membranes in the peripheral nervous system, Two principal classes of adrenergic receptors have been defined, the alpha-adrenergic receptors and the beta-adrenergic receptors. Five subtypes of adrenergic receptors ( a-1, a-2, b-1, b-2, and b-3 adrenergic receptors) have now been distinguished. The genes encoding these receptors have been isolated and identified (Cotecchia et al., 1988, Proc. Natl. Acad. Sci. USA 85: 7159–7163; Kobilka et al., 1987, Science 238: 650–656; Frielle et al., 1987, Proc. Natl. Acad. Sci. USA 84: 7920–7924; Emorine et al., 1987, Proc. Natl. Acad. Sci. USA 84: 6995–6999; Emorine et al., 1989, Science 245: 1118–1121). Analysis of these genes has made it possible to recognize that they belong to a family of integral membrane receptors exhibiting some homology (Dixon et al., 1998, Annual Reports in Medicinal Chemistry, 221–223; Emorine et al., 1988, Proc. NATO Adv. Res. Workshop), especially at portions of the seven transmembrane regions that are coupled to regulatory proteins, called G proteins, capable of binding molecules of guanosine triphosphate (GTP).

These membrane receptors, after they have bound the appropriate ligand (agonist or antagonist), are understood to undergo a conformational change that induces an intracellular signal that modifies the behavior of the target cell. Beta-adrenergic receptors catalyze the activation of a class of G proteins which in turn stimulates the activity of adenylate cyclase when they bind with catecholamine agonists, whereas alpha-adrenergic receptor antagonists act in competition with the agonists for the binding to the receptor and prevent the activation of adenylate cyclase. When adenylate cyclase is activated, it catalyses the production of an intracellular mediator or second messenger, especially cyclic AMP.

In the central nervous system, dopamine is a catecholamine neurotransmitter modulates neuronal cells involved in movement initiation, appetitive behavior, hormone release, and visual dark adaptation. In the periphery dopamine plays a role in modulating blood pressure and renal function (see generally Cooper et al., 1978, The Biochemical Basis of Neuropharmacology, 3d ed., Oxford University Press, New York, pp, 161–195). The diverse physiological actions of dopamine are in turn mediated by its interaction with a family of distinct dopamine receptors subtypes that are either "D1-like" or "D2-like," which respectively stimulate and inhibit the enzyme adenylate cyclase (Kebabian & Calne, 1979, Nature 277: 93–96). Alterations in the number or activity of these receptors may be a contributory factor in disease states such as Parkinson's disease (a movement disorder) and schizophrenia (a behavioral disorder) and attention deficit hyperactivity disorder (ADHD).

A great deal of information has accumulated regarding the biochemistry of the D1 and D2 dopamine receptors, and methods have been developed to solubilize and purify these receptor proteins (see Senogles et al., 1986, Biochemistry 25: 749–753; Sengoles et al., 1988, J. Biol. Chem. 263: 18996–19002; Gingrich et al., 1988, Biochemistry 27: 3907–3912). The D1 dopamine receptor in several tissues appears to be a glycosylated membrane protein of about 72 kD (Amlaiky et al., 1987, Mol. Pharmacol. 31: 129–134; Ninzik et al., 1988, Biochemistry 27: 7594–7599). The D2 receptor can also be glycosylated and has been suggested to have a higher molecular weight of about 90–150 kD (Amlaiky & Caron, 1985, J. Biol. Chem. 260: 1983–1986; Amlaiky & Caron, 1986, J. Neurochem. 47: 196–204; Jarvie et al., 1988, Mol. Pharmacol. 34: 91–97).

Dopamine receptors are primary targets in the clinical treatment of psycho-motor disorders such as Parkinson's disease and affective disorders such as schizophrenia (Seeman et al., 1987, *Neuropsychopharm.* 1: 5–15; Seeman, 1987, *Synapse* 1: 152–333). Five different dopamine receptor genes (D1, D2, D3, D4 and D5) and various splice variants of their transcripts have been cloned as a result of nucleotide sequence homology which exists between these receptor genes (Bunzow et al., 1988, *Nature* 336: 783–787; Grandy et al., 1989, *Proc. Natl. Acad. Sci. USA* 86: 9762–9766; Dal Toso et al., 1989, *EMBO J.* 8: 4025–4034; Zhou et al., 1990, *Nature* 346: 76–80; Sunahara et al., 1990, *Nature* 346: 80–83; Sokoloff et al., 1990, *Nature* 347: 146–151; Civelli et al., 1993, *Annu. Rev. Pharmacol. Toxicol.* 33: 281–307; Van Tol et al., 1991, *Nature* 350: 610–4).

Catecholamine receptors are also targets for a host of therapeutic agents for the treatment of shock, hypertension, arrhythmias, asthma, migraine headache, and anaphylactic reactions, and include antipsychotic drugs that are use to treat schizophrenia and β-blockers used to control high blood pressure.

The importance of catecholamine receptors, particularly in the brain and central nervous system, has created the need for the isolation of additional catecholamine receptors for the development of therapeutic agents for the treatment of disorders, including disorders of the CNS and most preferably treatment of disorders on mental health such as psychosis, in which catecholamines and their receptors have been implicated. There is also a need for developing new tools that will permit identification of new drug lead compounds for developing novel drugs. This is of particular importance for psychoactive and psychotropic drugs, due to their physiological importance and their potential to greatly benefit human patients treated with such drugs. At present, few such economical systems exist. Conventional screening methods require the use of animal brain slices in binding assays as a first step. This is suboptimal for a number of reasons, including interference in the binding assay by non-specific binding of heterologous (i.e., non-receptor) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human catecholamine receptor molecules in vitro would provide an efficient and economical means for rational drug design and rapid screening of potentially useful compounds. For these and other reasons, development of in vitro screening methods for psychotropic drugs has numerous advantages and is a major research goal in the pharmaceutical industry.

SUMMARY OF THE INVENTION

The present invention relates to the cloning, expression and functional characterization of a mammalian catecholamine receptor gene. The invention comprises nucleic acids having a nucleotide sequence of a novel mammalian catecholamine receptor gene. The nucleic acids provided by the invention comprise a complementary DNA (cDNA) copy of the corresponding mRNA transcribed in vivo from the catecholamine receptor genes of the invention. In one preferred embodiment, the mammalian catecholamine receptor is a human catecholamine receptor. In another preferred embodiment, the mammalian catecholamine receptor is a rat (*Rattus norvegicus*) catecholamine receptor. Also provided are the deduced amino acid sequence of the cognate proteins of the cDNAs provided by the invention, methods of making said cognate proteins by expressing the cDNAs in cells transformed with recombinant expression constructs comprising said cDNAs, and said recombinant expression constructs and cells transformed thereby.

This invention in a first aspect provides nucleic acids, nucleic acid hybridization probes, recombinant eukaryotic expression constructs capable of expressing the catecholamine receptors of the invention in cultures of transformed cells, and such cultures of transformed eukaryotic cells that synthesize the catecholamine receptors of the invention. In another aspect, the invention provides homogeneous compositions of the catecholamine receptor proteins of the invention, and membrane preparations from cells expressing the catecholamine receptor proteins of the invention, as well as antibodies against and epitopes of the catecholamine receptor proteins of the invention. The invention in another aspect provides methods for making said homogenous preparations and membrane preparations using cells transformed with the recombinant expression constructs of the invention and expressing said catecholamine receptor proteins thereby. Methods for characterizing the receptor and biochemical properties of these receptor proteins and methods for using these proteins in the development of agents having pharmacological uses related to these receptors are also provided by the invention.

In a first aspect, the invention provides a nucleic acid having a nucleotide sequence encoding a mammalian catecholamine receptor. In a first preferred embodiment, the nucleic acid encodes a human catecholamine receptor. In this embodiment of the invention, the nucleotide sequence comprises 1125 nucleotides of human catecholamine receptor cDNA comprising 1040 nucleotides of coding sequence, 20 nucleotides of 5' untranslated sequence and 85 nucleotides of 3' untranslated sequence. In this embodiment of the invention, the nucleotide sequence of the catecholamine receptor is the nucleotide sequence depicted in FIG. 1 (SEQ ID No:1). The sequence shown in FIG. 1 will be understood to represent one specific embodiment of a multiplicity of nucleotide sequences that encode the human catecholamine receptor amino acid sequence (SEQ ID No.: 2) of the invention and that these different nucleotide sequences are functionally equivalent and are intended to be encompassed by the claimed invention. In addition, it will be understood that different organisms and cells derived therefrom express preferentially certain tRNAs corresponding to subsets of the degenerate collection of tRNAs capable of encoding certain of the naturally-occurring amino acids, and that embodiments of the multiplicity of nucleotide sequences encoding the amino acid sequence of the human catecholamine receptor protein of the invention that are optimized for expression in specific prokaryotic and eukaryotic cells are also encompassed by the claimed invention. Isolated nucleic acid derived from human genomic DNA and isolated by conventional methods using the human cDNA provided by the invention is also within the scope of the claimed invention. Finally, it will be understood that allelic variations of the human catecholamine receptor, including naturally occurring and in vitro modifications thereof are within the scope of this invention. Each such variant will be understood to have essentially the same amino acid sequence as the sequence of the human catecholamine receptor disclosed herein.

In a second preferred embodiment of this aspect of the invention, the nucleic acid encodes the rat catecholamine receptor. In this embodiment of the invention, the nucleotide sequence includes 999 nucleotides of the rat catecholamine receptor cDNA comprising the coding sequence. In this embodiment of the invention, the nucleotide sequence of the catecholamine receptor is the nucleotide sequence depicted in FIG. 2 (SEQ ID No:3). The sequence shown in FIG. 2 will be understood to represent one specific embodiment of a multiplicity of nucleotide sequences that encode the rat catecholamine receptor amino acid sequence (SEQ ID No.: 4) of the invention and that these different nucleotide sequences are functionally equivalent and are intended to be encompassed by the claimed invention. In addition, it will be understood that different organisms and cells derived therefrom express preferentially certain tRNAs corresponding to subsets of the degenerate collection of tRNAs capable of encoding certain of the naturally-occurring amino acids, and that embodiments of the multiplicity of nucleotide sequences encoding the amino acid sequence of the rat catecholamine receptor protein of the invention that are optimized for expression in specific prokaryotic and eukaryotic cells are also encompassed by the claimed invention. Isolated nucleic acid derived from rat genomic DNA and isolated by conventional methods using the rat cDNA provided by the invention is also within the scope of the claimed invention. Finally, it will be understood that allelic variations of the rat catecholamine receptor, including naturally occurring and in vitro modifications thereof are within the scope of this invention. Each such variant will be understood to have essentially the same amino acid sequence as the sequence of the human catecholamine receptor disclosed herein.

Mammalian catecholamine receptor proteins corresponding to the human and rat cDNAs of the invention are a second aspect of the claimed invention. In a first embodiment, the mammalian catecholamine receptor protein is a human catecholamine receptor having a deduced amino acid sequence shown in FIG. 1 (SEQ ID No.:2). In a second embodiment is provided said human catecholamine receptor protein comprising a membrane preparation from a cell, most preferably a recombinant cell, expressing a nucleic acid encoding a human catecholamine of the invention. In a third embodiment, the mammalian catecholamine receptor protein is a rat catecholamine receptor having a deduced amino acid sequence shown in FIG. 2 (SEQ ID No.:4). In a fourth embodiment is provided said rat catecholamine receptor protein comprising a membrane preparation from a cell, most preferably a recombinant cell, expressing a nucleic acid encoding a rat catecholamine of the invention.

As provided in this aspect of the invention is a homogeneous composition of a mammalian catecholamine receptor having a molecular weight of about 39 kD or derivative thereof that is a human catecholamine receptor having an amino acid sequence shown in FIG. 1 and identified by SEQ ID No.:2, said size being understood to be the predicted size of the protein before any post-translational modifications thereof. Also provided is a homogeneous composition of a mammalian catecholamine receptor having a molecular weight of about 38 kD or derivative thereof that is a rat catecholamine receptor having an amino acid sequence shown in FIG. 2 and identified by SEQ ID No.:4, said size being understood to be the predicted size of the protein before any post-translational modifications thereof.

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clone of the invention encoding a mammalian catecholamine receptor or fragment thereof, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of the catecholamine receptor gene in various tissues of mammals, including humans. It is also an object of the present invention to provide nucleic acid hybridization probes derived from the sequences of mammalian catecholamine receptor genes of the invention to be used for the detection and diagnosis of genetic diseases. It is an object of this invention to provide nucleic acid hybridization probes derived from the nucleic acid sequences of the mammalian catecholamine receptor genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of catecholamine receptor-specific antibodies, or useful as competitors of catecholamine receptor molecules for agonist, antagonist or drug binding, or to be used for the production of inhibitors of the binding of agonists or antagonists or analogues thereof to such catecholamine receptor molecules.

The present invention also provides antibodies against and epitopes of the mammalian catecholamine receptormolecules of the invention. It is an object of thepresent invention to provide antibodies that are immunologically reactive to the catecholamine receptors of the invention. It is a particular object to provide monoclonal antibodies against these catecholamine receptors. Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with a cell line which expresses antigens or epitopes of a mammalian catecholamine receptor of the invention. The present invention also provides hybridoma cell lines that produce such antibodies, and can be injected into a living mouse to provide an ascites fluid from the mouse that is comprised of such antibodies. It is a further object of the invention to provide immunologically-active epitopes of the mammalian catecholamine receptorproteins of the invention. Chimeric antibodies immunologically reactive against the catecholamine receptor proteins of the invention are also within the scope of this invention.

The present invention provides recombinant expression constructs comprising a nucleic acid encoding a mammalian catecholamine receptor of the invention wherein the construct is capable of expressing the encoded catecholamine receptor in cultures of cells transformed with the construct. A preferred embodiment of such constructs comprises a human catecholamine receptor cDNA depicted in FIG. 1 (SEQ ID No.:1), such constructs being capable of expressing the human catecholamine receptor encoded therein in cells transformed with the construct. Another preferred embodiment of such constructs comprises a rat catecholamine receptor cDNA depicted in FIG. 2 (SEQ ID No.:3), such constructs being capable of expressing the human catecholamine receptor encoded therein in cells transformed with the construct.

The invention also provides prokaryotic and more preferably eukaryotic cells transformed with the recombinant expression constructs of the invention, each such cells being capable of and indeed expressing the mammalian catecholamine receptor encoded in the transforming construct, as well as methods for preparing mammalian catecholamine receptor proteins using said transformed cells.

The present invention also includes within its scope protein preparations of prokaryotic and eukaryotic cell membranes containing the catecholamine receptor protein of the invention, derived from cultures of prokaryotic or eukaryotic cells, respectively, transformed with the recombinant expression constructs of the invention.

The invention also provides methods for screening compounds for their ability to inhibit, facilitate or modulate the biochemical activity of the mammalian catecholamine receptor molecules of the invention, for use in the in vitro screening of novel agonist and antagonist compounds. In preferred embodiments, cells transformed with a recombinant expression construct of the invention are contacted with such a compound, and the binding capacity of the compounds, as well as the effect of the compound on binding of other, known catecholamine receptor agonists and antagonists, is assayed. Additional preferred embodiments comprise quantitative analyses of such effects.

The present invention is also useful for the detection of analogues, agonists or antagonists, known or unknown, of the mammalian catecholamine receptors of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIG. 1 illustrates the nucleotide (SEQ ID No.:1) and amino acid (SEQ ID No.:2) sequences of a human catecholamine receptor.

FIG. 2 illustrates the nucleotide (SEQ ID No.:3) and amino acid (SEQ ID No.:4) sequences of a rat catecholamine receptor.

FIG. 3 presents an amino acid sequence comparison between the human catecholamine receptor protein of the invention and human D1 dopamine receptor, human D2 dopamine receptor, rat serotonin 1c receptor, rat $a_{1-b}$ adrenergic receptor, rat serotonin 4 receptor, rat serotonin 1a receptor, human $a_2$-adrenergic receptor, and human H-2 histamine receptor in the putative transmembrane regions.

DETAILED DESCRIPTION OF THE PREFERRED EMBODIMENTS

Figure 4:
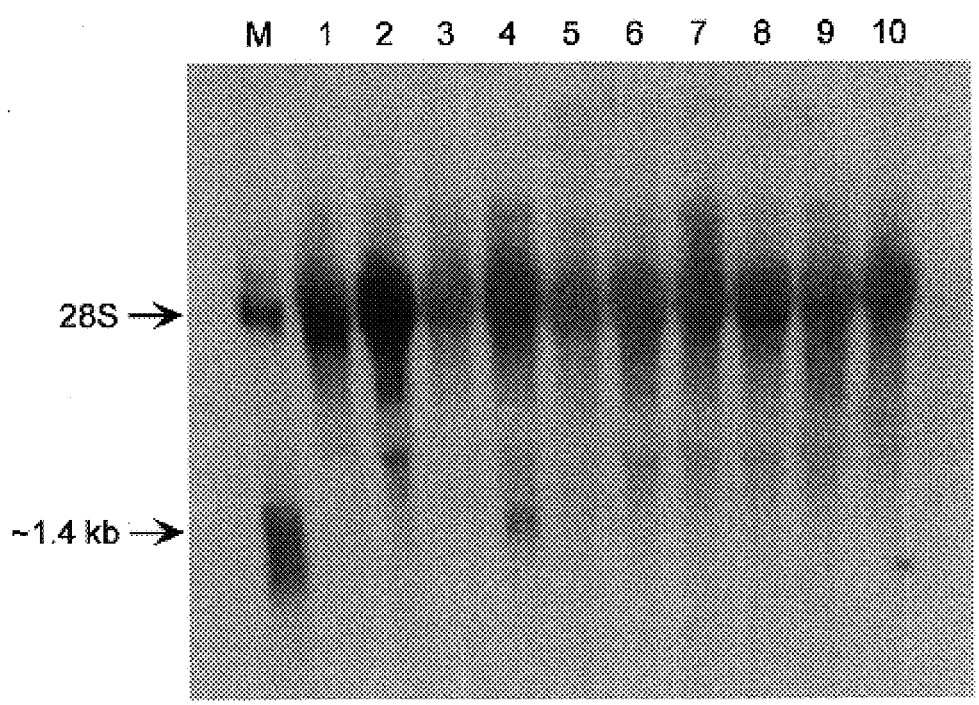
FIG. 4 is a photograph of an autoradiogram of Northern analysis of total cellular RNA (20 µg/lane) from human HEK293 cells expressing the human catecholamine receptor of the invention after transformation with a recombinant expression construct.

The term "mammalian catecholamine receptor" as used herein refers to proteins consisting essentially of, and having substantially the same biological activity as, the protein encoded by the amino acid depicted in FIG. 1 (SEQ ID No.:2) and FIG. 2 (SEQ ID No.: 4). This definition is intended to encompass natural allelic variations in the disclosed catecholamine receptor. Cloned nucleic acid provided by the present invention may encode catecholamine receptor protein of any species of origin, including, for example, mouse, rat, rabbit, cat, and human, but preferably the nucleic acid provided by the invention encodes catecholamine receptors of mammalian, most preferably rat and human, origin.

The nucleic acids provided by the invention comprise DNA or RNA having a nucleotide sequence encoding a mammalian catecholamine receptor. Specific embodiments of said nucleic acids are depicted in FIG. 1 (SEQ ID No.:1) or FIG. 2 (SEQ ID No.: 3), and include any nucleotide sequence encoding a mammalian catecholamine receptor having an amino acid sequence as depicted in FIG. 1 (SEQ ID No.: 2) or FIG. 2 (SEQ ID No.: 4). Nucleic hybridization probes as provided by the invention comprise any portion of a nucleic acid of the invention effective in nucleic acid hybridization under stringency conditions sufficient for specific hybridization. Mixtures of such nucleic acid hybridization probes are also within the scope of this embodiment of the invention. Nucleic acid probes as provided herein are useful for isolating mammalian species analogues of the specific embodiments of the nucleic acids provided by the invention. Nucleic acid probes as provided herein are. also useful for detecting mammalian catecholamine receptor gene expression in cells and tissues using techniques well-known in the art, including but not limited to Northern blot hybridization, in situ hybridization and Southern hybridization to reverse transcriptase-polymerase chain reaction product DNAs. The probes provided by the present invention, including oligonucleotides probes derived therefrom, are also useful for Southern hybridization of mammalian, preferably human, genomic DNA for screening for restriction fragment length polymorphism (RFLP) associated with certain genetic disorders.

The production of proteins such as mammalian catecholamine receptors from cloned genes by genetic engineering means is well known in this art. The discussion which follows is accordingly intended as an overview of this field, and is not intended to reflect the full state of the art.

Nucleic acid encoding a catecholamine receptor may be obtained, in view of the instant disclosure, by chemical synthesis, by screening reverse transcripts of mRNA from appropriate cells or cell line cultures, by screening genomic libraries from appropriate cells, or by combinations of these procedures, in accordance with known procedures as illustrated below. Screening of mRNA or genomic DNA may be carried out with oligonucleotide probes generated from the nucleic acid sequence information from mammalian catecholamine receptor nucleic acid as disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, mammalian catecholamine receptor nucleic acid sequences may be obtained by use of the polymerase chain reaction (PCR) procedure, using PCR oligonucleotide primers corresponding to nucleic acid sequence information derived from a catecholamine receptor as provided herein. See U.S. Pat. No. 4,683,195 to Mullis et al. and U.S. Pat. No. 4,683,202 to Mullis.

Mammalian catecholamine receptor protein may be synthesized in host cells transformed with a recombinant expression construct comprising a nucleic acid encoding the catecholamine receptor nucleic acid, comprising genomic DNA or cDNA. Such recombinant expression constructs can also be comprised of a vector that is a replicable DNA construct. Vectors are used herein either to amplify DNA encoding a catecholamine receptor and/or to express DNA encoding a catecholamine receptor gene. For the purposes of this invention, a recombinant expression construct is a replicable DNA construct in which a nucleic acid encoding a catecholamine receptor is operably linked to suitable control sequences capable of effecting the expression of the catecholamine receptor in a suitable host.

The need for such control sequences will vary depending upon the host selected and the transformation method chosen. Generally, control sequences include a transcriptional promoter, an optional operator or enhancer sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage and mammalian DNA and RNA viruses), retroviruses, and integratable DNA fragments (i.e., fragments integratable into the host genome by homologous recombination). The vector can replicate the gene of interest and function independently of the host genome, or can, in some instances, integrate into the genome itself Suitable vectors will contain replicon and control sequences which are derived from species compatible with the intended expression host. A preferred vector is RcRSV (obtained from Invitrogen, San Diego, Calif.). Transformed host cells are cells which have been transformed or transfected with recombinant expression constructs made using recombinant DNA techniques and comprising nucleic acid encoding a catecholamine receptor protein. Preferred host cells are HEK293 cells, COS-7 cells (Gluzman, 1981, *Cell* 23: 175–182) and Ltk⁻ cells. Transformed host cells may express the catecholamine receptor protein, but host cells transformed for purposes of cloning or amplifying nucleic acid hybridization probe DNA need not express the receptor. When expressed, the catecholamine receptor of the invention will typically be located in the host cell membrane. Accordingly, the invention provides preparations of said cell membranes comprising the catecholamine receptor protein of the invention, as well as purified, homogeneous preparations of the receptor protein itself. See, Sambrook et al., ibid.

Cultures of cells derived from multicellular organisms are a desirable host for recombinant catecholamine receptor protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human embryonic kidney (HEK) 293 cells, VERO and HeLa cells, Chinese hamster ovary (CHO) cell lines, mouse Ltk⁻ cell lines and WI138, BHK, COS-7, CV, and MDCK cell lines. HEK293 cell, COS-7 cells and Ltk⁻ cells are preferred.

The invention provides homogeneous compositions of mammalian catecholamine receptor protein produced by transformed eukaryotic cells as provided herein. Each such homogeneous composition is intended to be comprised of a catecholamine receptor protein that comprises at least 75%, more preferably at least 80%, and most preferably at least 90% of the protein in such a homogenous composition; in said homogeneous preparations, individual contaminating protein species are expected to comprise less than 5%, more preferably less than 2% and most preferably less than 1% of the preparation. The invention also provides membrane preparations from cells expressing mammalian catecholamine receptor protein as the result of transformation with a recombinant expression construct, as described herein.

Mammalian catecholamine receptor proteins made from cloned genes in accordance with the present invention may be used for screening catecholamine analogues, or catecholamine receptor agonists or antagonists of catecholamine binding, or for determining the amount of such agonists or antagonists are present in a solution of interest (e.g., blood plasma, cerebrospinal fluid or serum). For example, host cells may be transformed with a recombinant expression construct of the present invention, a mammalian catecholamine receptor expressed in those host cells, and the cells or membranes thereof used to screen compounds for their effect on catecholamine receptor agonist binding activity. By selection of host cells that do not ordinarily express a catecholamine receptor, pure preparations of membranes containing the receptor can be obtained.

The recombinant expression constructs of the present invention are useful in molecular biology to transform cells which do not ordinarily express a catecholamine receptor to thereafter express this receptor. Such cells are useful as intermediates for making cell membrane preparations useful for receptor binding activity assays, which are in turn useful for drug screening. The recombinant expression constructs of the present invention thus provide a method for screening potentially useful drugs at advantageously lower cost than conventional animal screening protocols. While not completely eliminating the need for ultimate in vivo activity and toxicology assays, the constructs and cultures of the invention provide an important first screening step for the vast number of potentially useful drugs synthesized, discovered or extracted from natural sources each year.

The recombinant expression constructs of the present invention are useful in molecular biology to detect, isolate, characterize and identify novel endogenous catecholamine receptor agonists and antagonists found in plasma, serum, lymph, cerebrospinal fluid, seminal fluid, or other potential sources of such compounds. This utility thereby enables rational drug design of novel therapeutically-active drugs using currently-available techniques (see Walters, "Computer-Assisted Modeling ofDrugs", in Klegerman & Groves, eds., 1993, *Pharmaceutical Biotechnology*, Interpharm Press:Buffalo Grove, Ill, pp. 165–174).

The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, *Cell* 51: 503–512; Bertling, 1987, Bioscience Reports 7: 107–112; Smithies et al., 1985, *Nature* 317: 230–234.

Nucleic acid and oligonucleotide probes as provided by the present invention are useful as diagnostic tools for probing catecholamine receptor gene expression in tissues of humans and other animals. For example, tissues are probed in situ with oligonucleotide probes carrying detectable groups by conventional autoradiographic or other detection techniques, to investigate native expression of this receptor or pathological conditions relating thereto. Further, chromosomes can be probed to investigate the presence or absence of the corresponding catecholamine receptor gene, and potential pathological conditions related thereto.

The invention also provides antibodies that are immunologically reactive to the catecholamine receptor protein or epitopes thereof provided by the invention. The antibodies provided by the invention may be raised, using methods well known in the art, in animals by inoculation with cells that express a catecholamine receptor or epitopes thereof, cell membranes from such cells, whether crude membrane preparations or membranes purified using methods well known in the art, or purified preparations of proteins, including fusion proteins, particularly fusion proteins comprising epitopes of the catecholamine receptor protein of the invention fused to heterologous proteins and expressed using genetic engineering means in bacterial, yeast or eukaryotic cells, said proteins being isolated from such cells to varying degrees of homogeneity using conventional biochemical methods. Synthetic peptides made using established synthetic methods in vitro and optionally conjugated with heterologous sequences of amino acids, are also encompassed in these methods to produce the antibodies of the invention. Animals that are useful for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses the catecholamine receptor provided by the invention, or more preferably any cell or cell line that expresses the catecholamine receptor of the invention, or any epitope thereof, as a result of molecular or genetic engineering, or that has been treated to increase the expression of an endogenous or heterologous catecholamine receptor protein by physical, biochemical or genetic means. Preferred cells are mammalian cells, most preferably cells syngeneic with a rodent, most preferably a mouse host, that have been transformed with a recombinant expression construct of the invention encoding a catecholamine receptor protein, and that express the receptor therefrom.

The present invention also provides monoclonal antibodies that are immunologically reactive with an epitope derived from a catecholamine receptor of the invention, or fragment thereof, present on the surface of such cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing a catecbolamine receptor of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid receptor of the invention. The present invention also encompasses fragments, including but not limited to F(ab) and F(ab)'$_2$ fragments, of such antibody. Fragments are produced by any number of methods, including but not limited to proteolytic or chemical cleavage, chemical synthesis or preparation of such fragments by means of genetic engineering technology. The present invention also encompasses single-chain antibodies that are immunologically reactive with an epitope of a catecholamine receptor, made by methods known to those of skill in the art.

The present invention also encompasses an epitope of a catecholamine receptor of the invention, comprised of sequences and/or a conformation of sequences present in the receptor molecule. This epitope may be naturally occurring, or may be the result of chemical or proteolytic cleavage of a receptor molecule and isolation of an epitope-containing peptide or may be obtained by chemical or in vitro synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to a catecholamine receptor-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of a Mammalian Catecholamine Receptor Probe by Random PCR Amplification of Rat Insulinoma cDNA Using Degenerate Oligonucleotide Primers In order to clone novel mammalian G-protein coupled receptors, cDNA prepared from total cellular RNA obtained from a rat pancreatic tumor cell line (AR42J (ATCC Accession No. CRL-1492) was used as template for a polymerase chain reaction (PCR)-based random cloning experiment. PCR was performed using a pair of degenerate oligonucleotide primers corresponding to a consensus sequence of the third and sixth transmembrane regions of known G-coupled receptors. PCR products obtained in this experiment were characterized by nucleotide sequencing. A full length clone was obtained by screening a rat genomic library using a cloned PCR product encoding a novel G-protein coupled receptor as deduced by nucleotide sequencing and comparison with a sequence database (GenBank).

The PCR amplification experiments were performed as follows. Total RNA was isolated from AR42J cells by the guanidinium thiocyanate method (Chirgwin et al., 1979, Biochemistry 18: 5294–5299). First-strand cDNA was prepared from this RNA using standard techniques (see Sambrook et al., 1990, *Molecular Cloning: A Laboratory Manual*, Cold Spring Harbor Press, Cold Spring Harbor Laboratory, N.Y.) using murine reverse transcriptase (BRL, Gaithersburg, Md.) and oligo-dT priming (Sambrook et al., ibid.). The rat cDNA preparation was then subjected to 35 cycles of PCR amplification using 500 picomoles of degenerate oligonucleotide primers having the following sequence:

Primer III (sense):

GAGTCGACCTGTG(C/T)G(C/T)(C/G)AT(C/T)(A/G)CIIT(G/T)GAC(C/A)G(C/G)TAC (SEQ ID NO:5) and Primer VI (antisense):

CAGAATTCAG(T/A)AGGGCAICCAGCAGAI(G/C)(G/A)(T/C)GAA (SEQ ID NO:6) in 30 μL of a solution containing 50 mM Tris-HCl (pH 8.3), 2.5 mM MgCl$_2$, 0.01% gelatin, 250 μM each dNTP, and 2.5 units of Taq polymerase (Saiki et al., 1988, Science 239: 487–491). Each PCR amplification cycle consisted of incubations at 94° C. for 90 sec (denaturation), 50° C. for 90 sec (annealing), and 72° C. for 120 sec (extension) for 35 cycles.

Amplified products of the PCR reaction were separated on a 1.0% agarose gel (see Sambrook et al., ibid.), and fragments ranging in size from 400 basepairs (bps) to 750 bp were subcloned in the plasmid vector pBluescript (Stratagene, LaJolla, Calif.). Plasmid DNA from these clones was purified and the nucleotide sequence of the insert cDNA determined by the dideoxynucleotide chain termination method (Sanger et al., 1977, Proc. Natl. Acad. Sci. USA 74: 5463–5467) using Sequenase® (U.S. Biochemical Corp., Cleveland, Ohio). PCR products were identified by screening the GenBank database and identified a cloned fragment having a high degree of homology to known catecholamine receptors, as well as containing sequence motifs that are common to the G-protein coupled family of receptors, but that was not identical to any previously-identified catecholamine receptor sequence.

EXAMPLE 2

Isolation of a Novel Mammalian Catecholamine Receptor cDNA

The cloned PCR product obtained in Example 1 was used to isolate a full-length clone from a rat genomic DNA library (obtained from Clonetech, Palo Alto, Calif.) as follows.

The 0.4 kb DNA fragment generated by PCR which has high homology to the known catecholamine receptors was $^{32}$P-labeled using the random priming technique (Stratagene, San Diego Calif.). This probe was used to screen a rat genomic library which had been transferred to nylon membranes (Gene Screen Plus, NEN, Boston Mass.). Hybridization was performed in 50% formamide, 5X SSC, 1% SDS, 5X Denhardt' solution, and salmon sperm DNA (50 μg/mL) with the radioactive probe at 2×10$^6$ cpm/mL at 37° C. for overnight. The nylon filters were then washed as follows: at room temperature in a solution of 2X SSC/0.1% SDS for 10 minutes, followed by a wash at 55° C. in a solution of 2X SSC/0.1% SDS for 15 minutes, and finally a wash at 55° C. in a solution of 0.5X SSC/0.1% SDS for 5 minutes. Filters were then exposed to XOMAT X-ray film (Kodak) overnight. Filter hybridization was performed in duplicate to confirm positive signals. Secondary and tertiary screens were performed until single homogenous clones were isolated.

This isolated genomic clone was then subjected to nucleotide sequence analysis. Nucleotide sequence analysis performed essentially as described in Example 1, and revealed the sequence of the rat catecholamine receptor shown in FIG. 2 (SEQ ID No.: 3). The putative protein product of the gene is also shown in FIG. 2 (SEQ ID No:4). The sequence was found to have an open reading frame comprising 996 nucleotides encoding a protein 332 amino acids in length, and having a predicted molecular weight of about 38 kD kilodaltons prior to post-translational modification. The sequence immediately 5' to the proposed initiation codon was found to contain several translation termination codons in-frame with the open reading frame, supporting the assignment of the translation start site. Predicted transmembrane domains (using the algorithm of Eisenberg et al. (1984, J. Molec. Biol. 179: 125–142)) are boxed and identified by Roman numerals (I–VII), and two sites of possible N-linked glycosylation are identified in the amino-terminal portion of the protein with solid triangles. Surprisingly, no potential protein phosphorylation sites were found in predicted cytoplasmic loops, unlike other known G-protein coupled receptors. On the basis of this analysis, this cloned nucleic acid was determined to be a novel mammalian catecholamine receptor.

Comparison of the amino acid sequence of the novel receptor with the amino acid sequences of other known mammalian catecholamine receptors supported this conclusion. The predicted amino acid sequences of the transmembrane domains of the novel catecholamine receptor were compared with the corresponding sequences in human D1 dopamine receptor, human D2 dopamine receptor, rat serotonin 1c receptor, rat α1-b adrenergic receptor, rat serotonin 4 receptor, rat serotonin 1a receptor, human a-2 adrenergic receptor, and human H-2 histamine receptor; the results of these comparisons are shown in FIG. 3 (Probst et al., 1992, DNA Cell Biology 11: 1–20). Overbars indicate predicted transmembrane regions I through VII in the protein product of the genes. Amino acid residues that are found in common between the different mammalian catecholamine receptors are presented in boldface.

A more detailed comparison of these amino acid sequences are quantified in Table I, showing the percentage extent of homology in pairwise fashion between the different catecholamine receptors.

TABLE I

| Receptor | % Identity |
|---|---|
| human D1 dopamine | 40 |
| human D2 dopamine | 37 |
| rat α1-b adrenergic | 37 |
| rat serotonin 1c | 35 |
| rat α1-b adrenergic | 35 |
| rat serotonin 4 | 35 |
| rat serotonin 1a | 34 |
| human α2 adrenergic | 33 |
| human H-2 histamine | 33 |

Comparisons are made individually at each transmembrane domain (TMI–TMVII), as an average over all transmembrane domains (TM avg) and as the average degree of amino acid sequence homology for each protein as a whole (avg/all). These result support the conclusion that the novel mammalian receptor disclosed herein is a catecholamine receptor. In addition, the certain amino acid residues in other G-protein coupled receptors (such as Asp$^{103}$ in TM III) were also found in the novel cloned receptor described herein. These data are consistent with the fact that the catecholamine receptors have a significantly higher homology to the novel receptor disclosed herein than any other members of the G-protein coupled receptor family. The sequence DRY (amino acids 120–123 in the human sequence and amino acids 119–122 in the rat sequence) is conserved in the majority of G-protein coupled receptors. Expression of this receptor in a rat insulinoma suggests that catecholamines may play a role in pancreatic cell function.

EXAMPLE 3

Construction of a Recombinant Expression Constructs, DNA Transfection and Functional Expression of the Novel Mammalian Catecholamine Receptor In order to biochemically characterize the novel mammalian (rat) catecholamine receptor described in Example 2, and to confirm that it encodes a novel catecholamine receptor, the rat cDNA was cloned into a mammalian expression construct (pRcRSVneo, obtained from Invitrogen, San Diego, Calif.), the resulting recombinant expression construct transfected into COS-7 cells (for transient expression assays) and human embryonic kidney cells (HEK293) for stable expression assays, and cell membranes (COS-7) or cell lines (HEK293) were generated that expressed the receptor protein in cellular membranes at the cell surface. Such cells and membranes isolated from such cells were used for biochemical characterization experiments described below.

The entire coding region of the receptor DNA insert was amplified using PCR as described above with primers specific for flanking sequences; such PCR primers advantageously contained restriction enzyme digestion recognition sites at the 5' termini such that digestion with said restriction enzymes allowed facile cloning of the receptor cDNA into the RcRSVneo mammalian expression construct. PCR products generated in this way were subcloned in to the RcRSV vector using conventional techniques (see Sambrook et al., ibid.) and the orientation of the inserted cDNA confirmed by restriction enzyme digestion analysis of insert-containing subclones. Such recombinant expression constructs were introduced into COS-7 cells using the calcium-phosphate precipitation technique (Chen & Okayama, 1987, Molec. Cell. Biol. 7: 2745–2752), the transfected cells allowed to express the receptor for between 24–96 hours, and then cell membranes containing the receptor were isolated. Such membranes were harvested from cells grown on 15 cm plates by pelleting the cells at 20,000 rpm in a solution of 50 mM Tris-HCl (pH 7.4). The protein concentration was adjusted to 15–80 μg/sample for each of the binding studies described below.

These recombinant expression constructs were also introduced into HEK293 cells using the calcium-phosphate precipitation technique, and stably-transfected clones were selected by growth in the mammalian neomycin analog G418 (Grand Island Biological Co., Long Island, N.Y.), as the vector RcRSV contains a functional copy of a bacterial neomycin resistance gene. Stable cell lines were then selected for membrane binding studies based on mRNA expression levels of individual neomycin-resistant transfected clones determined by Northern analysis (see Sambrook et al., ibid.). Cell membranes were prepared and used as described above for COS-7 cell transfectants.

Expression of the catecholamine receptor gene in transfected cells was verified by Northern blot analysis of individual transfectants, performed using conventional techniques. Total cellular was extracted from transfected cells using and RNA Easy kit (obtained from Qiagen, Valencia, Calif.). For Northern hybridization, 10 μg of total cellular RNA was subjected to electrophoresis in a 1.2% agarose gel using HEPES/EDTA buffer (pH 7.8) overnight. The electrophoresed RNA was then transferred to a GeneScreen Plus membrane (New England Nuclear, Boston, Mass.) by capillary transfer, and fixed to the membrane by baking at 85° C. for 1 h. The membrane was then prehybridized overnight at 37° C. in the following buffer: 50% formamide, 1% sodium dodecyl sulfate (SDS), 5X SSC (where 1X SSC is 0.15M NaCl/0.015M sodium citrate, pH 7), 50 µg/mL denatured salmon sperm DNA, and 5X P-buffer (comprising 0.25M Tris, pH 7.5, 0.5% sodium pyrophosphate, 0.5% SDS, 1% bovine serum albumin, 1% polyvinylpyrrolidone and 1% Ficoll (400,000 MW)). After prehybridization, $^{32}$P-labeled DNA prepared from the full-length genomic receptor clone described above was added at a concentration of 3×10$^6$ cpm/mL and the membrane hybridized overnight at 37° C. The hybridized membrane was then washed using the following high-stringency washing conditions: 10 min at room temperature in a wash solution of 2X SSC/1% SDS; 10 min at 60° C. in 2X SSC/1% SDS; and finally 5 min at 60° C. in 0.5X SC/1% SDS, where the washing solutions were changed between each washing step. The washed membrane was then exposed overnight to X-ray film (X-omat, Kodak, Rochester, N.Y.).

The results of these experiments are shown in FIG. 4. As shown in the photograph, the transfected catecholamine receptor is expressed in transfected HEK293 cells.

Specific binding assays using a variety of catecholamine receptor agonists and antagonists were performed on membranes from both transient and stable transfectants. Ligand binding experiments were performed essentially as described in Bunzow et al. (1988, Nature 336: 783–787). In binding experiments, increasing amounts of membrane protein (from 15–80 µg) was incubated with each of the radioactively-labeled catecholamine agonist or antagonist to be tested for 120 min at 22° C. in a total volume of 1 mL.

EXAMPLE 4

Distribution of Catecholamine Receptor Expression in Mammalian Cell Lines, Rat Brain and Peripheral Tissues The distribution of mRNA corresponding to expression of the catecholamine receptor gene in various regions of the rat brain was determined by reverse transcription/polymerase chain reaction (RT-PCR) performed as follows. Total RNA from various rat brain sections was isolated using the RNA Easy kit (Qiagen) described in Example 3 and converted to single-stranded cDNA using reverse transcriptase (BRL, Gaithersburg, Md.) primed by oligo dT or random primers or a combination of both these primers. PCR was then performed using the 5' sense primer (TCT CTG AGT GAT GCA TCT TTG; SEQ ID No. 7) corresponding to the 5' extent of the receptor coding sequence and either an antisense primer (AGC AGT GCT CAA CTG TTC TCA CCA TGC; SEQ ID No.: 8) having its 3' end at nucleotide residue 243 of the SEQ ID No. 3 (resulting in a PCR product of about 250 bp in length) or an antisense primer (GCA CGA TTA ATT GAC CTC GCT TG; SEQ ID No.: 9) having its 3' end at nucleotide residue 650 of the SEQ ID No. 3 (resulting in a PCR product of about 650 bp in length). Using either primer pair, PCR was performed for 35 cycles, wherein one cycle consisted of incubations at 94° C. for 90 sec (denaturation), 55° C. for 90 sec (annealing), and 72° C. for 120 sec (extension).

The resulting fragments were resolved from 30 µL reaction mixture using 1% agarose gel electrophoresis and visualized by ethidium bromide staining and UV illumination. The fragments were then transferred onto a nylon membrane (GeneScreen Plus, NEN) by capillary transfer and hybridized under high stringency conditions as described above with a $^{32}$P-labeled probe prepared from the full-length rat genomic clone encoding the novel catecholamine receptor of the invention as described herein. Hybridized fragments were detected using a phosphoimager (Molecular Devices, Mountain View, Calif.).

Figure 5A:
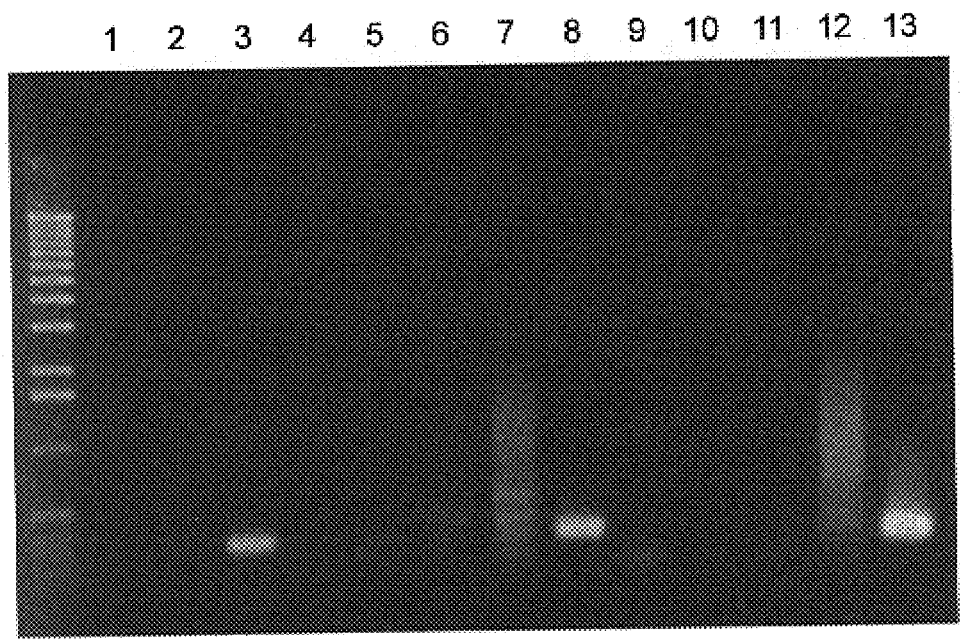
FIG. 5A is a photograph of an ethidium bromide-stained and ultraviolet light irradiated agarose gel containing DNA fragments produced by RT-PCR of RNA from rat brain tissues. The PCR products resolved on this gel are from the following rat brain regions, from which cDNA was synthesized from oligo(dT)-primed total RNA: lane 1, pituitary gland; lane 2, hindbrain; lane 3, midbrain; lane 4, locus coeruleus; lane 5, hypothalamus; lane 6, striatum; lane 7, olfactory bulb; lane 8, olfactory tubercle; lane 9, hippocampus; lane 10, cortex; lane 11, cerebellum; lane 12, thalamus; lane 13, 1:100 dilution of human catecholamine plasmid DNA.
Figure 5B:
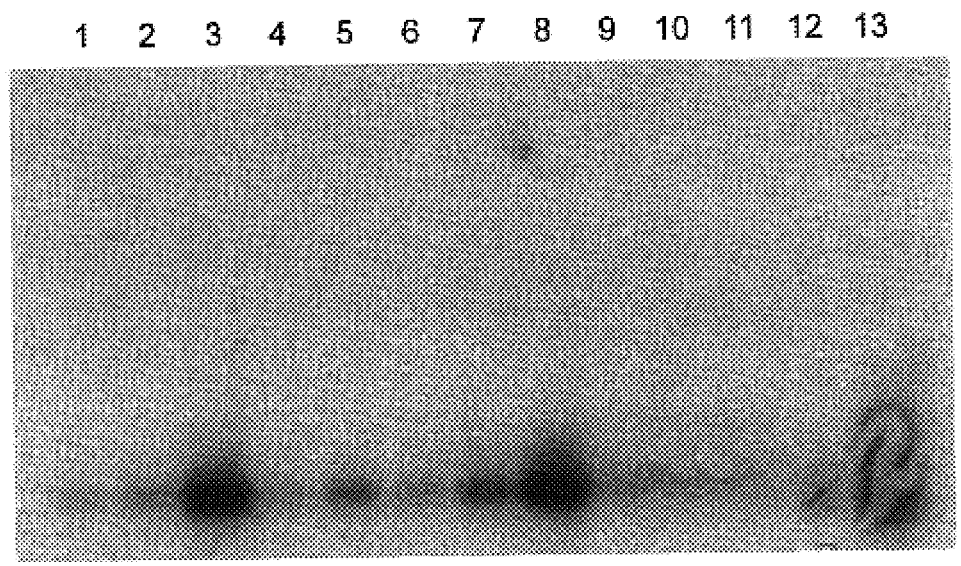
FIG. 5B is an autoradiogram of a nylon membrane containing DNA fragments transferred from the agarose gel shown in FIG. 5A and probed with $^{32}$P-labeled nucleic acid prepared from the coding sequence of the rat genomic clone encoding the rat catecholamine receptor of the invention.

The results of these experiments are shown in FIGS. 5A and 5B. FIG. 5A shows a photograph of an ethidium bromide stained 1% agarose gel viewed under ultraviolet light illumination. PCR product (10 µL of a 30 µL reaction mixture) was electrophoresed as described above, and bands specific for the predicted fragments of the rat catecholamine receptor of the invention (250 or 650 bp) were detected. FIG. 5B shows the results of the hybridization assay, which results in greater sensitivity of detection of PCR-amplified fragments. These results indicated that the catecholamine receptor was expressed strongly in midbrain and olfactory tubercle, less strongly in the olfactory bulb, moderately in the striatum and weakly in the hypothalamus.

Figure 6:
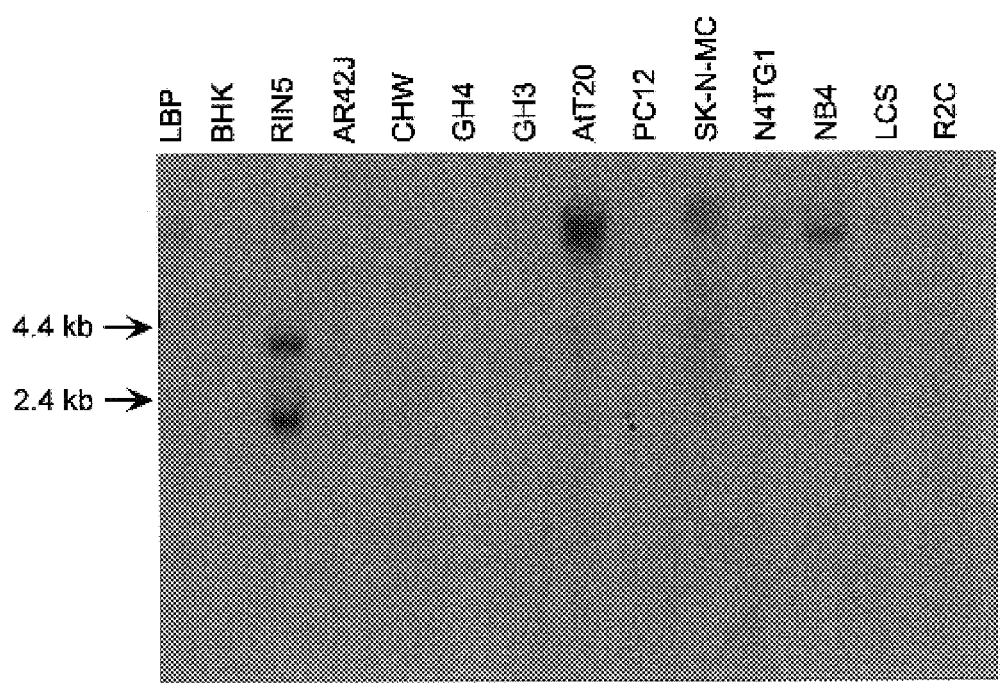
FIG. 6 is a photograph of an autoradiogram of Northern analysis of RNA from various rat cell lines expressing the rat catecholamine receptor of the invention after transfection with a recombinant expression construct encoding the rat catecholamine receptor. RNA shown in this gel was obtained from the following cell lines: lane 1, LBP; lane 2, baby hamster kidney (BHK) cells; lane 3, rat insulinoma (RIN5) cells; lane 4, AR42J rat pancreatic tumor cell line; lane 5, CHW cells; lane 6, GH4 rat pituitary cells; lane 7, GH3 rat pituitary cells; lane 8, AtT20 rat pituitary cells; lane 9, PC 12 rat adrenal gland cells; lane 10, SK-N-MC human neuroblastoma cells; lane 11, N4TG1 rat neuroblastoma cells; lane 12, NB4 cells; lane 13, LCS cells; lane 14, R2C rat Ledig cells.
Figure 7:
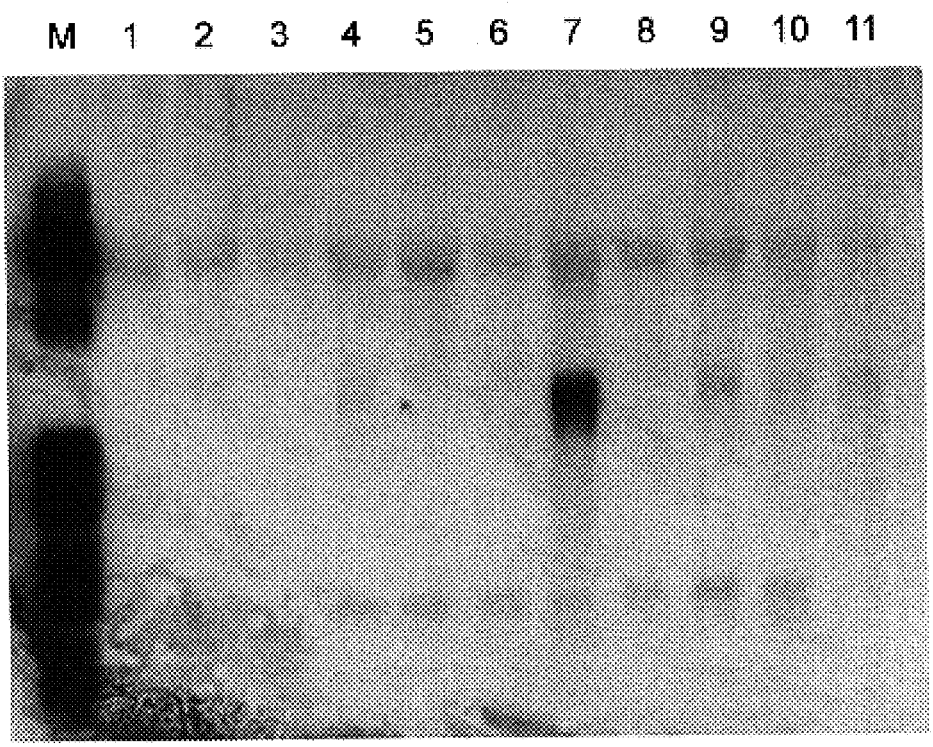
FIG. 7 is a photograph of an autoradiogram of Northern analysis of mRNA expressed in various cell lines expressing a mammalian catecholamine receptor of the invention after transfection with a recombinant expression construct encoding the rat catecholamine receptor.

Northern analysis of total RNA was performed as described in Example 2 above to detect catecholamine receptor expression in various established mammalian cell lines. These results are shown in FIG. 6. Expression of the catecholamine receptor gene of the invention was detected only in rat insulinoma cell line RIN5, while the AR42J cell line from which the cloned cDNA was obtained did not show a signal in this experiment, indicating it was present only at low levels and could not be detected in a Northern blot prepared from total cellular RNA (i.e., not having been enriched for mRNA, for example, by selection with oligo (dT)).

Figure 8A:
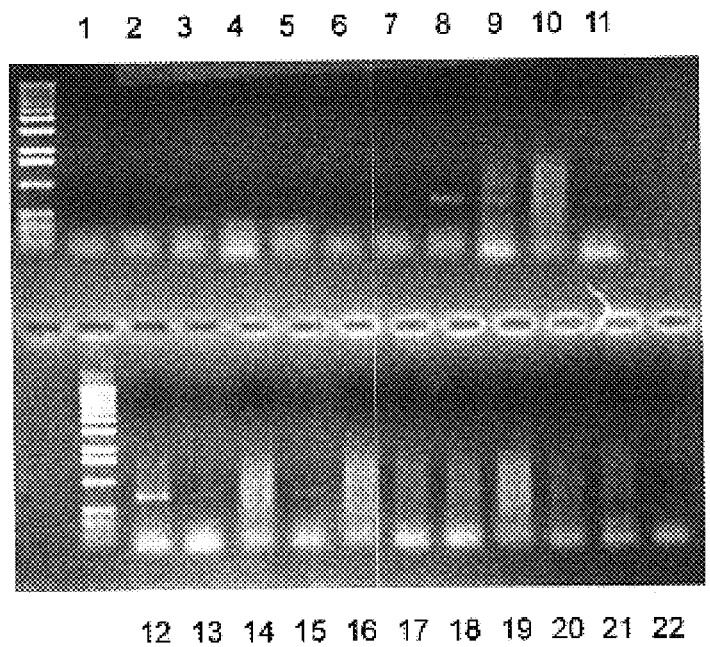
FIG. 8A is a photograph of an ethidium bromide-stained and ultraviolet light irradiated agarose gel containing DNA fragments produced by RT-PCR of RNA from rat tissues. The PCR products resolved on this gel are from the following rat tissues: lane 1, livei (oligo(dT) primed); lane 2, brain (dT); lane 3, spleen (dT); lane 4, lung (dT); lane 5, heart (dT); lane 6, testis (dT); lane 7, kidney (dT); lane 8, intestine (dT); lane 9, COS-7 cell oligo(dT)-selected mRNA from cells transformed with the RC-RSV/rat catecholamine receptor construct of the invention; lane 10, striatum (dT); lane 11, midbrain (random primed; rp); lane 12, olfactory tubercle (rp); lane 13, cortex (rp+dT); lane 14, midbrain (dT); lane 15, olfactory tubercle (rp); lane 16, olfactory bulb (dT); lane 17, hippocampus (dT); lane 18, midbrain (dT); lane 19, thalamus (dT); lane 20, striatum (dT); lane 21, olfactory bulb (dT); lane 22, water (negative control).
Figure 8B:
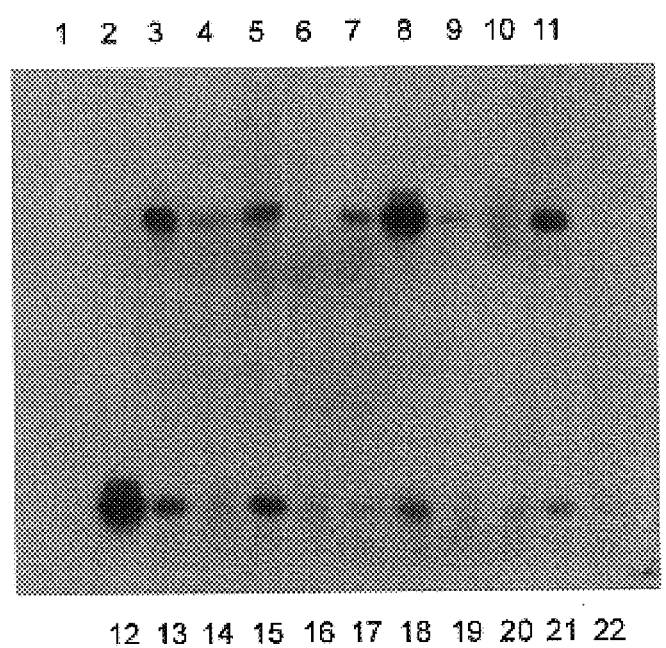
FIG. 8B is an autoradiogram of a nylon membrane containing DNA fragments transferred from the agarose gel shown in FIG. 8A and probed with $^{32}$P-labeled nucleic acid prepared from the full-length rat genomic clone encoding the rat catecholamine receptor of the invention.

The results of RT-PCR analysis performed on mRNA obtained from various rat tissues as described above are shown in FIG. 8A, and hybridization analysis of these results is shown in FIG. 8B to increase detection of PCR-amplified fragments. These results indicated the following pattern of catecholamine receptor expression in these tissues:

olfactory tubercle>intestine≧midbrain, cortex, spleen>heart, kidney

The receptor was also expressed at detectable levels in lung, transfected COS cells, and olfactory bulb. These results are consistent with known patterns of catecholamine receptor expression in olfactory tubercle and midbrain.

EXAMPLE 5

Cloning the Human Catecholamine Receptor Gene

The novel mammalian catecholamine receptor cDNA obtained in Example 2 was used to isolate a partial genomic clone from a library of human genomic DNA cloned in lambda EMBL3 (obtained from Clontech, Palo Alto, Calif.) as follows. The full-length rat receptor cDNA (~1 kb in length) was $^{32}$P-labeled by the random priming technique a kit obtained from Stratagene (San Diego, Calif.) according to the manufacturer's instructions. This probe was then used to screen the human genomic library which had been plated and then transferred to nylon membranes (Gene Screen Plus, NEN, Boston, Mass.). Hybridization was performed in a solution of 50% formamide, 5X SSC, 1% SDS, 5X Denhardt solution, and salmon sperm DNA (50 micrograms/mL) with the radioactive probe at 2×10$^6$ cpm/mL and at a temperature of 37° C. overnight. The nylon filters were then washed at room temperature in a solution of 2X SSC/0.1% SDS for 10 minutes, followed by a wash at 55° C. in a solution of 2X SSC/0.1% SDS for 15 minutes, and finally awash at 55° C. in a solution of 0.5X SSC/0.1% SDS for 5 minutes. Filters were then exposed to XOMAT X-ray film (Kodak) overnight at −80° C. Filter hybridization was performed in duplicate to confirm positive signals. Secondary and tertiary screens were performed until single homogenous clones were identified.

Individual genomic clones were then isolated and the nucleotide sequence determined. The nucleotide sequence analysis, performed essentially as described in Example 1, revealed that the longest insert contained a partial N-terminal sequence of the human homologue of the rat catecholamine receptor. Based on this information a set of oligonucleotide primers were synthesized having the following sequence:
Primer VII (sense):

5' TTGACAGCCCTCAGGAATGATG 3' (SEQ. ID: NO:10) and

Primer VIII (antisense):

5' ATGGAAAATGGAGGCTGAGCTCAG 3' (SEQ. ID NO:11)

These primers were then used to identify a bacterial artificial chromosome (BAC) clone encoding the entire human catecholamine receptor gene. Pools of BAC DNA obtained from Research Genetics (Release IV, Catalogue #96011) were subjected to PCR in a 30 micoliter solution that contained primers VII and VIII in addition to 50 mM Tris-HCl (pH 8.3), 2.5 mM $MgCl_2$, 0.01% gelatin, 250 $\mu$M each dNTP, and 2.5 units of Taq polymerase (Saiki et al., 1988, Science 239: 487–491). Each PCR amplification cycle consisted of incubations at 94° C. for 90 sec (denaturation), 50° C. for 90 sec (annealing), and 72° C. for 120 sec (extension) for 35 cycles.

Amplified products of the PCR reaction were separated on a 1.0% agarose gel (see Sambrook et al., ibid.). Fragments of the expected size (630 bp) were subcloned into the plasmid vector pBluescript (Stratagene, LaJolla, Calif.) and sequence analysis of the inserts confirmed that the BAC contained the human catecholamine receptor gene of interest. To obtain the complete DNA sequence of the novel human catecholamine receptor gene sense oligonucleotide primers were designed based on the sequence information obtained from the BAC and EMBL3 clones. The resulting sequence information was then used in the design of additional primers. This process wasa repeated until the end of the coding region was reached.

Consistent with its rat homologue the novel human catecholamine receptor is encoded by a single coding exon. The sequence of the human receptor is presented in FIG. 1. Interestingly, the open reading frame of the human homologue of the catecholamine receptor gene is 21 bases longer than the rat (1017 vs 996, respectively) which translates into a human receptor that is 339 amino acids long compared to a receptor of 332 amino acids in the rat (shown in FIG. 2). A comparison between the primary amino acid sequences of the human and rat receptors is presented in FIG. 3.

EXAMPLE 6

Chromosomal Mapping of the Genomic Locus of the Human Catecholamine Receptor Gene The chromosomal locus of the human catecholamine receptor gene of the invention was mapped by fluorescence in situ hybridization as follows.

BAC DNA encoding the human catecholaine receptor described in Example 5 was nick-translated using digoxigenin-11-UTP for use as a probe for in situ chromosomal mapping to localize the gene. This fluorescently labeled DNA was hybridized in situ to denatured human metaphase chromosomes for 16 hours. Signal was detected in the presence of DAPI (4,6-diamidino-2-phenylindole) counter staining and the chromosome was identified by sequential G-banding. The hybridization signal appeared to be consistent with a chromosomal location on the distal long arm of chromosome 6. By alignment of the hybridized metaphases with an ideogram of chromosome 6 (at the 400 band stage), the human catecholamine receptor gene was assigned to the locus 6q23.

Figure 9A:
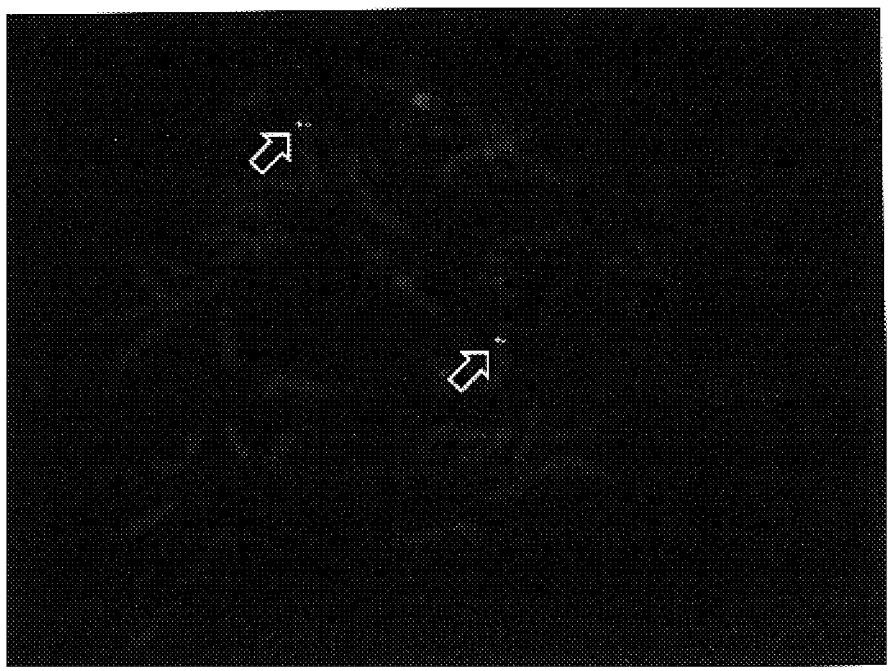
FIGS. 9A through 9D are photographs of fluorescence in situ hybridization analysis of human chromosomes probed with a fluorescently-labeled human artificial chromosome (BAC) containing the human catecholamine receptor DNA (BAC obtained from Research Genetics, Release IV of DNA pools, Catalog #96001; clone address: plate 278, Row D, Column 22).
Figure 9B:
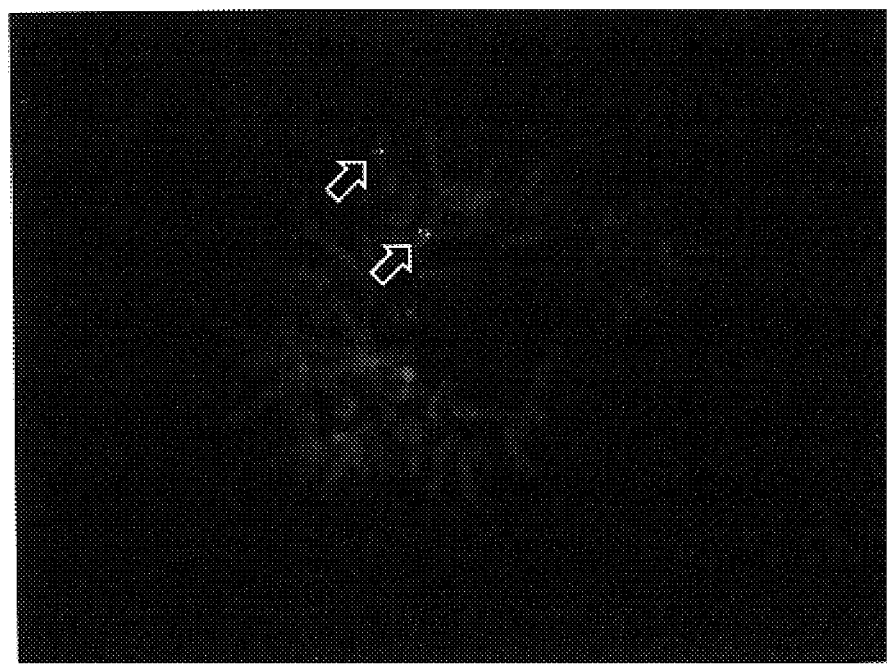
Figure 9C:
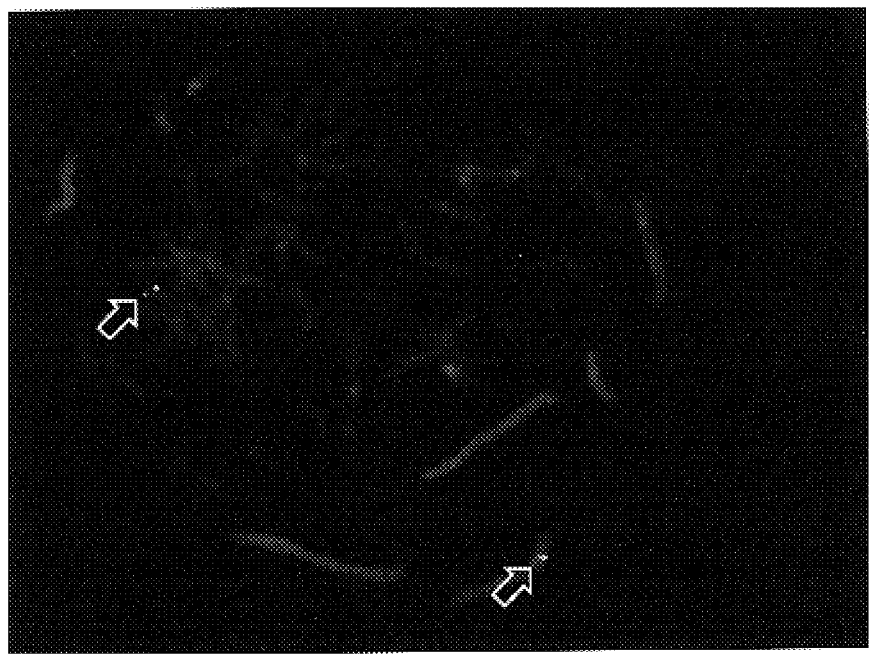
Figure 9D:
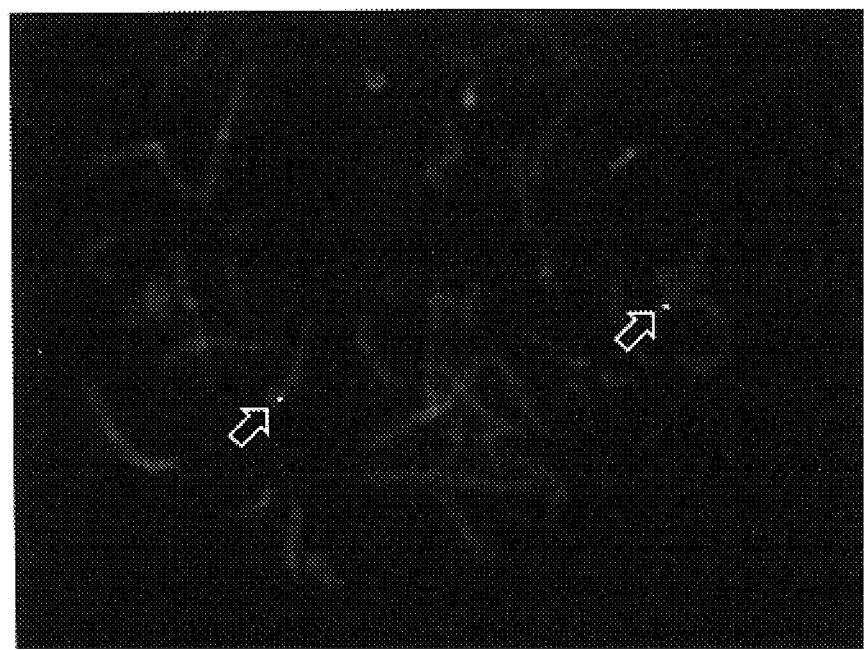
Figure 9E:
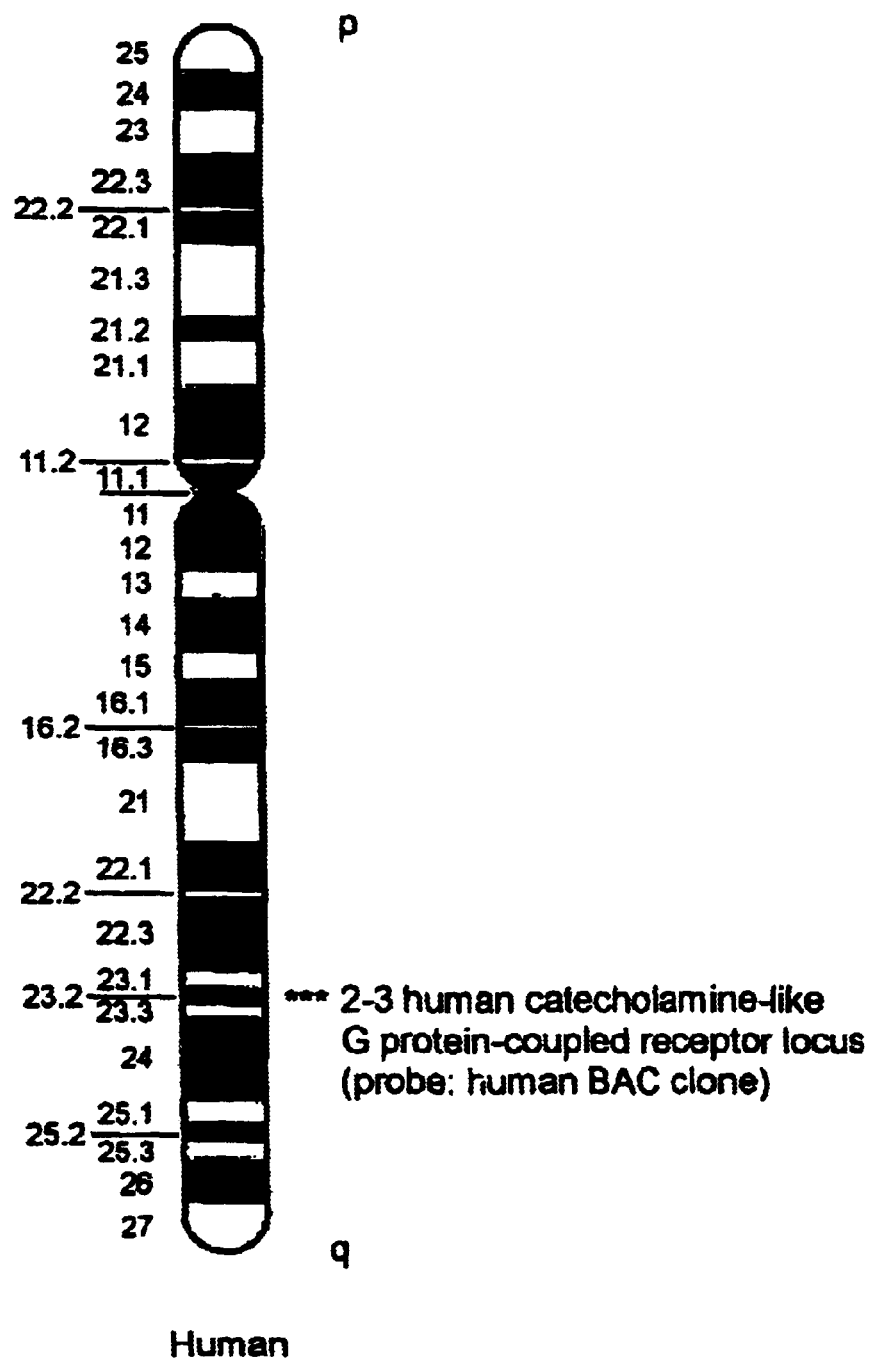
FIG. 9E is a schematic diagram of human chromosome 6 denoting the location of the human catecholamine locus at 6q23.2.

The results of these experiments are shown in FIGS. 9A through 9D, and a schematic representation of these results is shown in FIG. 9E. As can be seen in these Figures, the human catecholamine receptor gene corresponding to the cDNA provided by the invention was mapped to human chromosome 6, specifically at 6q23.2.

EXAMPLE 7

Detection of MAP Kinase Pathway Stimulation by the Human Catecholamine Receptor Gene It has been determined that G-protein coupled receptors are capable of stimulating the MAP (microtubule-associated protein) kinase assay in mammalian cells. The recognition of this role of G-protein coupled receptors has facilitated the development of an assay for testing the response of G-protein coupled receptors to potential ligands in vitro, thereby simplifying characterization of said receptors.

In this assay, activation of the pathway by ligand binding to receptor results in increased phosphorylation of mammalian transcription factor Elk by the MK kinase. The phosphorylated Elk transcription factor then binds to promoters containing cis-sequences responsive to this transcription factor. Transcription factor binding results in increase transcription of sequences operatively linked and under the transcriptional control of such Elk-responsive promoters. Most advantageously, reporter genes, such as β-galactosidase or firefly luciferase are operatively linked to such Elk-responsive promoters, thereby permitting ligand binding to a receptor to be linked with expression of the reporter gene.

HEK 293 cells were transfected with the full-length human clone encoding the catecholamine receptor of the invention contained in the pcDNA 3.1 expression vector (Invitrogen), wherein the first 22 nucleotides of the 5' untranslated region is followed by an initiation codon (ATG, Met), followed by nucleotides encoding an 8-amino acid FLAG sequence (Asp-Tyr-Lys-Asp-Asp-Asp-Asp-Lys; SEQ ID No.: 12), followed by a nucleotide sequence encoding the 21 amino acids of the human D2 receptor (as disclosed in co-owned U.S. Pat. No. 5,880,260, issued Mar. 9, 1999, incorporated by reference in its entirety herein) that follow the Met initiation codon in the native D2 sequence, which is followed by the complete sequence of the human catecholamine receptor; this construct was termed H2-3pcDNA3.1.

Control cells were transfected with pcDNA3.1 without the rat catecholamine receptor sequences. All cells were also co-transfected with 2 additional constructs: one (elk-gal) that encoded the yeast transcription factorgal under the transcriptional control of an Elk-responsive promoter; and another encoding firefly luciferase under the transcriptional control of a gal-responsive promoter. In cells containing the rat catecholamine-encoding construct, ligand binding to the receptor expressed thereby activated the map kinase (MK) pathway, which results in phosphorylation of the endogenous Elk transcription factor. In its phosphorylated state, Elk interacts with the elk DNA binding site and leads to activation of transcription of the gal gene contained in the elk-gal plasmid. In turn, transcription of the luciferase gene is activated in the co-transfected luciferase construct. Luciferase transciption was quantified using a luminometer, and gave an indirect measure of MK activation by each ligand. The results of these experiments as shown in Table II, showing the fold stimulation for each potential ligand compared with cells incubated in the absence of the ligand.

TABLE II

| Ligand | H2-3 pcDNA3.1 | pcDNA3.1 |
| --- | --- | --- |
| Dopamine | 1.21 | 1.04 |
| Serotonin | 1.22 | 1 |
| Norepinephrine | 1.69 | 1.3 |
| Clonidine[1] | 1.47 | 1.07 |
| SKF82958[2] | 2.52 | 0.79 |
| ADTN67[3] | 1.93 | 0.78 |
| Quinpirole[3] | 2.14 | 0.6 |

TABLE II-continued

| Ligand | H2-3 pcDNA3.1 | pcDNA3.1 |
| --- | --- | --- |

[1] $\alpha_2$-adrenergic and imidazoline receptor agonist
[2] D1 dopamine receptor agonist
[3] $\alpha$-2 adrenergic receptor agonist These results indicate that the cloned rat genomic DNA disclosed herein encodes a receptor that is specifically activated by drugs that target certain catecholamine receptors. However, the profile for this activation does not correspond to that for any of the known catecholamine receptors, indicating that this is a novel, brain-specific, catecholamine-binding receptor having a unique pharmacology useful thereby as a therapeutic target.

It should be understood that the foregoing disclosure emphasizes certain specific embodiments of the invention and that all modifications or alternatives equivalent thereto are within the spirit and scope of the invention as set forth in the appended claims.

What we claim is:

1. An isolated nucleic acid comprising a nucleotide sequence encoding a mammalian catecholamine receptor, wherein the mammalian catecholamine receptor is a human catecholamine receptor and the nucleic acid encodes an amino acid sequence identified by SEQ ID No.:2.

2. An isolated nucleic acid comprising a nucleotide sequence identified by SEQ ID NO: 1.

3. A recombinant expression construct comprising an isolated nucleic acid having a nucleotide sequence encoding a mammalian catecholamine receptor according to claim 1, wherein the construct is capable of expressing the receptor in a transformed culture of eukaryotic or prokaryotic cells.

4. A cell culture transformed with the recombinant expression construct of claim 3, wherein the transformed cell culture expresses the mammalian catecholamine receptor.

5. An isolated nucleic acid comprising a nucleotide sequence encoding a mammalian catecholamine receptor that hybridizes to a nucleic acid having a nucleotide sequence identified by SEQ ID NO: 1, under conditions of 37° C. in a buffer comprising 50% formamide, 1% sodium dodecyl sulfate, 5X SSC, 50 µg/mL denatured salmon sperm DNA, and 5X P-buffer comprising 0.25M Tris, pH 7.5, 0.5% sodium pyrophosphate, 0.5% SDS, 1% bovine serum albumin, 1% polyvinylpyrrolidone and 1% Ficoll.

6. An isolated nucleic acid according to claim 5, wherein the nucleic acid hybridizes to a nucleic acid having a nucleotide sequence identified by SEQ ID NO: 1, under washing conditions of 10 minutes at room temperature in a wash solution of 2X SSC/1% SDS, followed by 10 min at 60° C. in 2X SSC/1% SDS, followed by 5 min at 60° C. in 0.5X SC/1% SDS.

7. An isolated nucleic acid comprising a nucleotide sequence encoding a mammalian catecholamine receptor that hybridizes to a nucleic acid having a nucleotide sequence identified by SEQ ID NO: 3, under conditions of 37° C. in a buffer comprising 50% formamide, 1% sodium dodecyl sulfate, 5X SSC, 50 µg/mL denatured salmon sperm DNA, and 5X P-buffer comprising 0.25M Tris, pH 7.5, 0.5% sodium pyrophosphate, 0.5% SDS, 1% bovine serum albumin, 1% polyvinylpyrrolidone and 1% Ficoll.

* * * * *

UNITED STATES PATENT AND TRADEMARK OFFICE
CERTIFICATE OF CORRECTION

PATENT NO.    : 6,783,973 B1
DATED         : August 31, 2004
INVENTOR(S)   : James R. Bunzow and David K. Grandy It is certified that error appears in the above-identified patent and that said Letters Patent is hereby corrected as shown below:

<u>Title page,</u>
Item [57], ABSTRACT,
Line 7, delete "catecholarnine" and insert therefor -- catecholamine --.

<u>Column 34,</u>
Line 28, delete "0.5X SC/1% SDS." and insert therefor -- 0.5X SSC/1% SDS. --.

Signed and Sealed this

Fifth Day of April, 2005

JON W. DUDAS
*Director of the United States Patent and Trademark Office*

SEQUENCE LISTING

<160> NUMBER OF SEQ ID NOS: 12

<210> SEQ ID NO 1
<211> LENGTH: 1125
<212> TYPE: DNA
<213> ORGANISM: Homo sapiens
<220> FEATURE:
<221> NAME/KEY: CDS
<222> LOCATION: (21)..(1037)

<400> SEQUENCE: 1

```
ctaattgaca gccctcagga atg atg ccc ttt tgc cac aat ata att aat att      53
                      Met Met Pro Phe Cys His Asn Ile Ile Asn Ile
                       1               5                  10 tcc tgt gtg aaa aac aac tgg tca aat gat gtc cgt gct tcc ctg tac     101
Ser Cys Val Lys Asn Asn Trp Ser Asn Asp Val Arg Ala Ser Leu Tyr
            15                  20                  25 agt tta atg gtg ctc ata att ctg acc aca ctc gtt ggc aat ctg ata     149
Ser Leu Met Val Leu Ile Ile Leu Thr Thr Leu Val Gly Asn Leu Ile
        30                  35                  40 gtt att gtt tct ata tca cac ttc aaa caa ctt cat acc cca aca aat     197
Val Ile Val Ser Ile Ser His Phe Lys Gln Leu His Thr Pro Thr Asn
    45                  50                  55 tgg ctc att cat tcc atg gcc act gtg gac ttt ctt ctg ggg tgt ctg     245
Trp Leu Ile His Ser Met Ala Thr Val Asp Phe Leu Leu Gly Cys Leu
60                  65                  70                  75 gtc atg cct tac agt atg gtg aga tct gct gag cac tgt tgg tat ttt     293
Val Met Pro Tyr Ser Met Val Arg Ser Ala Glu His Cys Trp Tyr Phe
                80                  85                  90 gga gaa gtc ttc tgt aaa att cac aca agc acc gac att atg ctg agc     341
Gly Glu Val Phe Cys Lys Ile His Thr Ser Thr Asp Ile Met Leu Ser
            95                  100                 105 tca gcc tcc att ttc cat ttg tct ttc atc tcc att gac cgc tac tat     389
Ser Ala Ser Ile Phe His Leu Ser Phe Ile Ser Ile Asp Arg Tyr Tyr
        110                 115                 120
```

```
gct gtg tgt gat cca ctg aga tat aaa gcc aag atg aat atc ttg gtt      437
Ala Val Cys Asp Pro Leu Arg Tyr Lys Ala Lys Met Asn Ile Leu Val
    125                 130                 135 att tgt gtg atg atc ttc att agt tgg agt gtc cct gct gtt ttt gca      485
Ile Cys Val Met Ile Phe Ile Ser Trp Ser Val Pro Ala Val Phe Ala
140                 145                 150                 155 ttt gga atg atc ttt ctg gag cta aac ttc aaa ggc gct gaa gag ata      533
Phe Gly Met Ile Phe Leu Glu Leu Asn Phe Lys Gly Ala Glu Glu Ile
                160                 165                 170 tat tac aaa cat gtt cac tgc aga gga ggt tgc ctc gtc ttc ttt agc      581
Tyr Tyr Lys His Val His Cys Arg Gly Gly Cys Leu Val Phe Phe Ser
            175                 180                 185 aaa ata tct ggg gta ctg acc ttt atg act tct ttt tat ata cct gga      629
Lys Ile Ser Gly Val Leu Thr Phe Met Thr Ser Phe Tyr Ile Pro Gly
        190                 195                 200 tct att atg tta tgt gtc tat tac aga ata tat ctt atc gct aaa gaa      677
Ser Ile Met Leu Cys Val Tyr Tyr Arg Ile Tyr Leu Ile Ala Lys Glu
    205                 210                 215 cag gca aga tta att agt gat gcc aat cag aag ctc caa att gga ttg      725
Gln Ala Arg Leu Ile Ser Asp Ala Asn Gln Lys Leu Gln Ile Gly Leu
220                 225                 230                 235 gaa atg aaa aat gga att tca caa agc aaa gaa agg aaa gct gtg aag      773
Glu Met Lys Asn Gly Ile Ser Gln Ser Lys Glu Arg Lys Ala Val Lys
                240                 245                 250 aca ttg ggg att gtg atg gga gtt ttc cta ata tgc tgg tgc cct ttc      821
Thr Leu Gly Ile Val Met Gly Val Phe Leu Ile Cys Trp Cys Pro Phe
            255                 260                 265 ttt atc tgt aca gtc atg gac cct ttt ctt cac tca att att cca cct      869
Phe Ile Cys Thr Val Met Asp Pro Phe Leu His Ser Ile Ile Pro Pro
        270                 275                 280 act ttg aat gat gta ttg att tgg ttt ggc tac ttg aac tct aca ttt      917
Thr Leu Asn Asp Val Leu Ile Trp Phe Gly Tyr Leu Asn Ser Thr Phe
    285                 290                 295 aat cca atg gtt tat gca ttt ttc tat cct tgg ttt aga aaa gca ctg      965
Asn Pro Met Val Tyr Ala Phe Phe Tyr Pro Trp Phe Arg Lys Ala Leu
300                 305                 310                 315 aag atg atg ctg ttt ggt aaa att ttc caa aaa gat tca tcc agg tgt     1013
Lys Met Met Leu Phe Gly Lys Ile Phe Gln Lys Asp Ser Ser Arg Cys
                320                 325                 330 aaa tta ttt ttg gaa ttg agt tca tagaattatt atatttact gttttgcaaa    1067
Lys Leu Phe Leu Glu Leu Ser Ser
            335 tcggttgatg atcatattta tgaacacaac ataacgaacc acatgcacca accacatg    1125

<210> SEQ ID NO 2
<211> LENGTH: 339
<212> TYPE: PRT
<213> ORGANISM: Homo sapiens

<400> SEQUENCE: 2

Met Met Pro Phe Cys His Asn Ile Ile Asn Ile Ser Cys Val Lys Asn
 1               5                  10                  15

Asn Trp Ser Asn Asp Val Arg Ala Ser Leu Tyr Ser Leu Met Val Leu
                20                  25                  30

Ile Ile Leu Thr Thr Leu Val Gly Asn Leu Ile Val Ile Val Ser Ile
            35                  40                  45

Ser His Phe Lys Gln Leu His Thr Pro Thr Asn Trp Leu Ile His Ser
        50                  55                  60

Met Ala Thr Val Asp Phe Leu Leu Gly Cys Leu Val Met Pro Tyr Ser
```

```
                65                  70                  75                  80
            Met Val Arg Ser Ala Glu His Cys Trp Tyr Phe Gly Glu Val Phe Cys
                            85                  90                  95
            Lys Ile His Thr Ser Thr Asp Ile Met Leu Ser Ser Ala Ser Ile Phe
                        100                 105                 110
            His Leu Ser Phe Ile Ser Ile Asp Arg Tyr Tyr Ala Val Cys Asp Pro
                        115                 120                 125
            Leu Arg Tyr Lys Ala Lys Met Asn Ile Leu Val Ile Cys Val Met Ile
                    130                 135                 140
            Phe Ile Ser Trp Ser Val Pro Ala Val Phe Ala Phe Gly Met Ile Phe
            145                 150                 155                 160
            Leu Glu Leu Asn Phe Lys Gly Ala Glu Glu Ile Tyr Tyr Lys His Val
                            165                 170                 175
            His Cys Arg Gly Gly Cys Leu Val Phe Phe Ser Lys Ile Ser Gly Val
                        180                 185                 190
            Leu Thr Phe Met Thr Ser Phe Tyr Ile Pro Gly Ser Ile Met Leu Cys
                        195                 200                 205
            Val Tyr Tyr Arg Ile Tyr Leu Ile Ala Lys Glu Gln Ala Arg Leu Ile
                    210                 215                 220
            Ser Asp Ala Asn Gln Lys Leu Gln Ile Gly Leu Glu Met Lys Asn Gly
            225                 230                 235                 240
            Ile Ser Gln Ser Lys Glu Arg Lys Ala Val Lys Thr Leu Gly Ile Val
                            245                 250                 255
            Met Gly Val Phe Leu Ile Cys Trp Cys Pro Phe Phe Ile Cys Thr Val
                        260                 265                 270
            Met Asp Pro Phe Leu His Ser Ile Ile Pro Pro Thr Leu Asn Asp Val
                        275                 280                 285
            Leu Ile Trp Phe Gly Tyr Leu Asn Ser Thr Phe Asn Pro Met Val Tyr
                    290                 295                 300
            Ala Phe Phe Tyr Pro Trp Phe Arg Lys Ala Leu Lys Met Met Leu Phe
            305                 310                 315                 320
            Gly Lys Ile Phe Gln Lys Asp Ser Ser Arg Cys Lys Leu Phe Leu Glu
                            325                 330                 335
            Leu Ser Ser

<210> SEQ ID NO 3
<211> LENGTH: 999
<212> TYPE: DNA
<213> ORGANISM: Rattus norvegicus
<220> FEATURE:
<221> NAME/KEY: CDS
<222> LOCATION: (1)..(996)

<400> SEQUENCE: 3 atg cat ctt tgc cac aat agc gcg aat att tcc cac acg aac agg aac        48
Met His Leu Cys His Asn Ser Ala Asn Ile Ser His Thr Asn Arg Asn
  1               5                  10                  15 tgg tca agg gat gtc cgt gct tca ctg tac agc tta ata tca ctc ata        96
Trp Ser Arg Asp Val Arg Ala Ser Leu Tyr Ser Leu Ile Ser Leu Ile
             20                  25                  30 att cta acc act ctg gtt ggc aac tta ata gta atc att tcg ata tcc       144
Ile Leu Thr Thr Leu Val Gly Asn Leu Ile Val Ile Ile Ser Ile Ser
         35                  40                  45 cac ttc aag caa att cac acg ccc aca aat tgg ctc ctt cat tcc atg       192
His Phe Lys Gln Ile His Thr Pro Thr Asn Trp Leu Leu His Ser Met
     50                  55                  60
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gcc | gtt | gtc | gac | ttt | ctg | ctg | ggc | tgt | ctg | gtc | atg | ccc | tac | agc | atg | 240 |
| Ala | Val | Val | Asp | Phe | Leu | Leu | Gly | Cys | Leu | Val | Met | Pro | Tyr | Ser | Met |     |
| 65  |     |     |     | 70  |     |     |     |     | 75  |     |     |     |     | 80  |     |     |

```
gcc gtt gtc gac ttt ctg ctg ggc tgt ctg gtc atg ccc tac agc atg        240
Ala Val Val Asp Phe Leu Leu Gly Cys Leu Val Met Pro Tyr Ser Met
 65              70                  75                  80 gtg aga aca gtt gag cac tgc tgg tac ttt ggg gaa ctc ttc tgc aaa        288
Val Arg Thr Val Glu His Cys Trp Tyr Phe Gly Glu Leu Phe Cys Lys
             85                  90                  95 ctt cac acc agc act gat atc atg ctg agc tcg gca tcc att ctc cac        336
Leu His Thr Ser Thr Asp Ile Met Leu Ser Ser Ala Ser Ile Leu His
            100                 105                 110 cta gcc ttc att tcc att gac cgc tac tat gct gtg tgc gac cct tta        384
Leu Ala Phe Ile Ser Ile Asp Arg Tyr Tyr Ala Val Cys Asp Pro Leu
        115                 120                 125 aga tac aaa gcc aag atc aat ctc gcc gcc att ttt gtg atg atc ctc        432
Arg Tyr Lys Ala Lys Ile Asn Leu Ala Ala Ile Phe Val Met Ile Leu
130                 135                 140 att agc tgg agc ctt cct gct gtt ttt gca ttt ggg atg atc ttc ctg        480
Ile Ser Trp Ser Leu Pro Ala Val Phe Ala Phe Gly Met Ile Phe Leu
145                 150                 155                 160 gag ctg aac tta gaa gga gtt gag gag cag tat cac aat cag gtc ttc        528
Glu Leu Asn Leu Glu Gly Val Glu Glu Gln Tyr His Asn Gln Val Phe
                165                 170                 175 tgc ctg cgc ggc tgt ttt cta ttc ttc agt aaa gta tct ggg gta ctg        576
Cys Leu Arg Gly Cys Phe Leu Phe Phe Ser Lys Val Ser Gly Val Leu
            180                 185                 190 gca ttc atg acg tct ttc tat ata cct ggg tct gtt atg tta ttt gtt        624
Ala Phe Met Thr Ser Phe Tyr Ile Pro Gly Ser Val Met Leu Phe Val
        195                 200                 205 tac tat gag ata tat ttc ata gct aaa gga caa gcg agg tca att aat        672
Tyr Tyr Glu Ile Tyr Phe Ile Ala Lys Gly Gln Ala Arg Ser Ile Asn
210                 215                 220 cgt gca aac ctt caa gtt gga ttg gaa ggg gaa agc aga gcg cca caa        720
Arg Ala Asn Leu Gln Val Gly Leu Glu Gly Glu Ser Arg Ala Pro Gln
225                 230                 235                 240 agc aag gaa aca aaa gcc gcg aaa acc tta ggg atc atg gtg ggc gtt        768
Ser Lys Glu Thr Lys Ala Ala Lys Thr Leu Gly Ile Met Val Gly Val
                245                 250                 255 ttc ctc ctg tgc tgg tgc ccg ttc ttt tgc atg gtc ctg gac cct            816
Phe Leu Leu Cys Trp Cys Pro Phe Phe Cys Met Val Leu Asp Pro
            260                 265                 270 ttc ctg ggc tat gtt atc cca ccc act ctg aat gac aca ctg aat tgg        864
Phe Leu Gly Tyr Val Ile Pro Pro Thr Leu Asn Asp Thr Leu Asn Trp
        275                 280                 285 ttc ggg tac ctg aac tct gcc ttc aac ccg atg gtt tat gcc ttt ttc        912
Phe Gly Tyr Leu Asn Ser Ala Phe Asn Pro Met Val Tyr Ala Phe Phe
    290                 295                 300 tat ccc tgg ttc aga aga gcg ttg aag atg gtt ctc ttc ggt aaa att        960
Tyr Pro Trp Phe Arg Arg Ala Leu Lys Met Val Leu Phe Gly Lys Ile
305                 310                 315                 320 ttc caa aaa gat tca tct agg tct aag tta ttt ttg taa                    999
Phe Gln Lys Asp Ser Ser Arg Ser Lys Leu Phe Leu
                325                 330

<210> SEQ ID NO 4
<211> LENGTH: 332
<212> TYPE: PRT
<213> ORGANISM: Rattus norvegicus

<400> SEQUENCE: 4

Met His Leu Cys His Asn Ser Ala Asn Ile Ser His Thr Asn Arg Asn
  1               5                  10                  15
```

```
Trp Ser Arg Asp Val Arg Ala Ser Leu Tyr Ser Leu Ile Ser Leu Ile
            20                  25                  30
Ile Leu Thr Thr Leu Val Gly Asn Leu Ile Val Ile Ile Ser Ile Ser
        35                  40                  45
His Phe Lys Gln Ile His Thr Pro Thr Asn Trp Leu Leu His Ser Met
    50                  55                  60
Ala Val Asp Phe Leu Leu Gly Cys Leu Val Met Pro Tyr Ser Met
65                  70                  75                  80
Val Arg Thr Val Glu His Cys Trp Tyr Phe Gly Glu Leu Phe Cys Lys
                85                  90                  95
Leu His Thr Ser Thr Asp Ile Met Leu Ser Ser Ala Ser Ile Leu His
            100                 105                 110
Leu Ala Phe Ile Ser Ile Asp Arg Tyr Tyr Ala Val Cys Asp Pro Leu
        115                 120                 125
Arg Tyr Lys Ala Lys Ile Asn Leu Ala Ala Ile Phe Val Met Ile Leu
130                 135                 140
Ile Ser Trp Ser Leu Pro Ala Val Phe Ala Phe Gly Met Ile Phe Leu
145                 150                 155                 160
Glu Leu Asn Leu Glu Gly Val Glu Glu Gln Tyr His Asn Gln Val Phe
                165                 170                 175
Cys Leu Arg Gly Cys Phe Leu Phe Phe Ser Lys Val Ser Gly Val Leu
            180                 185                 190
Ala Phe Met Thr Ser Phe Tyr Ile Pro Gly Ser Val Met Leu Phe Val
        195                 200                 205
Tyr Tyr Glu Ile Tyr Phe Ile Ala Lys Gly Gln Ala Arg Ser Ile Asn
    210                 215                 220
Arg Ala Asn Leu Gln Val Gly Leu Glu Gly Glu Ser Arg Ala Pro Gln
225                 230                 235                 240
Ser Lys Glu Thr Lys Ala Ala Lys Thr Leu Gly Ile Met Val Gly Val
                245                 250                 255
Phe Leu Leu Cys Trp Cys Pro Phe Phe Phe Cys Met Val Leu Asp Pro
            260                 265                 270
Phe Leu Gly Tyr Val Ile Pro Pro Thr Leu Asn Asp Thr Leu Asn Trp
        275                 280                 285
Phe Gly Tyr Leu Asn Ser Ala Phe Asn Pro Met Val Tyr Ala Phe Phe
    290                 295                 300
Tyr Pro Trp Phe Arg Arg Ala Leu Lys Met Val Leu Phe Gly Lys Ile
305                 310                 315                 320
Phe Gln Lys Asp Ser Ser Arg Ser Lys Leu Phe Leu
                325                 330

<210> SEQ ID NO 5
<211> LENGTH: 35
<212> TYPE: DNA
<213> ORGANISM: Artificial Sequence
<220> FEATURE:
<221> NAME/KEY: modified_base
<222> LOCATION: (23)..(24)
<223> OTHER INFORMATION: i
<223> OTHER INFORMATION: Description of Artificial Sequence:
      oligonucleotide primer

<400> SEQUENCE: 5
gagtcgacct gtgygysaty rcnntkgacm gstac                          35

<210> SEQ ID NO 6
<211> LENGTH: 33
```

```
<212> TYPE: DNA
<213> ORGANISM: Artificial Sequence
<220> FEATURE:
<221> NAME/KEY: modified_base
<222> LOCATION: (18)
<223> OTHER INFORMATION: i
<221> NAME/KEY: modified_base
<222> LOCATION: (28)
<223> OTHER INFORMATION: i
<223> OTHER INFORMATION: Description of Artificial Sequence:
      oligonucleotide primer

<400> SEQUENCE: 6
cagaattcag wagggcancc agcagansry gaa                          33

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 7
tctctgagtg atgcatcttt g                                       21

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
agcagtgctc aactgttctc accatgc                                 27

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
gcacgattaa ttgacctcgc ttg                                     23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 10
ttgacagccc tcaggaatga tg                                      22

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
```

-continued

```
atggaaaatg gaggctgagc tcag                                      24

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: FLAG
      sequence

<400> SEQUENCE: 12

Asp Tyr Lys Asp Asp Asp Asp Lys
 1               5
```